(12) United States Patent
Ostrovsky

(10) Patent No.: US 9,788,929 B2
(45) Date of Patent: Oct. 17, 2017

(54) DEVICES FOR DELIVERING IMPLANTS

(71) Applicant: Boston Scientific Scimed, Inc., Maple Grove, MN (US)

(72) Inventor: Isaac Ostrovsky, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 561 days.

(21) Appl. No.: 14/195,604

(22) Filed: Mar. 3, 2014

(65) Prior Publication Data

US 2014/0257022 A1 Sep. 11, 2014

Related U.S. Application Data

(60) Provisional application No. 61/773,966, filed on Mar. 7, 2013.

(51) Int. Cl.
*A61F 2/00* (2006.01)
*A61B 17/04* (2006.01)
(Continued)

(52) U.S. Cl.
CPC ........ *A61F 2/0045* (2013.01); *A61B 17/0482* (2013.01); *A61B 17/0483* (2013.01);
(Continued)

(58) Field of Classification Search
CPC ........... A61F 2/0045; A61F 2220/0075; A61B 17/0482; A61B 17/0483; A61B 17/0625;
(Continued)

(56) References Cited

U.S. PATENT DOCUMENTS

2010/0191038 A1* 7/2010 Kubalak .............. A61F 2/0045
600/30
2011/0306821 A1* 12/2011 Witzmann ......... A61B 17/0401
600/30
(Continued)

FOREIGN PATENT DOCUMENTS

| WO | 2009/075800 A1 | 6/2009 |
| WO | 2013/033373 A1 | 3/2013 |
| WO | 2014/138106 A2 | 9/2014 |

OTHER PUBLICATIONS

International Search Report and Written Opinion for PCT Application No. PCT/US2014/20386, mailed on Jun. 5, 2014, 10 pages.
(Continued)

*Primary Examiner* — Christine H Matthews
*Assistant Examiner* — Kaylee Wilson
(74) *Attorney, Agent, or Firm* — Brake Hughes Bellermann LLP

(57) ABSTRACT

This invention generally relates to devices and methods that allow an operator to deliver a suture and an implant coupled to the suture into the body of a patient without the need for direct-vision of the operator. In one aspect, a medical device includes a receiving arm that releasably holds an implant or suture in place for capture and a clamping arm that includes a needle deployment mechanism for advancing a needle directly to the implant for capture and for retracting the needle with the implant attached to deliver the implant into the desired location. The receiving arm includes a cavity with inner walls that are angled to direct the needle through the opening after the advancing needle pierces and goes through tissue of the patient. The angled walls facilitate movement of the needle into a position within the cavity where the implant gets engaged with the needle.

19 Claims, 31 Drawing Sheets

(51) Int. Cl.
    *A61B 17/062*     (2006.01)
    *A61B 17/06*     (2006.01)
    *A61B 17/00*     (2006.01)

(52) U.S. Cl.
    CPC .... *A61B 17/0625* (2013.01); *A61B 17/06109* (2013.01); *A61B 2017/00805* (2013.01); *A61B 2017/06042* (2013.01); *A61F 2220/0075* (2013.01)

(58) Field of Classification Search
    CPC .... A61B 17/06109; A61B 2017/00805; A61B 2017/06042
    USPC .............................. 606/139, 151; 600/30, 36
    See application file for complete search history.

(56) References Cited

U.S. PATENT DOCUMENTS

| | | | |
|---|---|---|---|
| 2012/0232573 A1 | 9/2012 | Ostrovsky et al. | |
| 2013/0060261 A1* | 3/2013 | Ostrovsky .......... | A61B 17/0469 606/139 |

OTHER PUBLICATIONS

International Preliminary Report on Patentability for PCT Application No. PCT/US2014/20386, mailed on Sep. 17, 2015, 9 pages.

\* cited by examiner

DEVICES FOR DELIVERING IMPLANTS

CROSS-REFERENCE TO RELATED APPLICATIONS

This application is a Nonprovisional of, and claims priority to, U.S. Patent Application No. 61/773,966, filed on Mar. 7, 2013, entitled "DEVICES FOR DELIVERING IMPLANTS", which is incorporated by reference herein in its entirety.

This application is related to co-owned and co-assigned U.S. Provisional Application No. 61/773,972, filed on Mar. 7, 2013, entitled "MEDICAL DEVICES AND IMPLANT ASSEMBLIES FOR IMPLANT CAPTURE", and U.S. application Ser. No. 13/416,488, filed on Mar. 9, 2012, entitled "MULTI-ARM INSIDE-OUT TOOL FOR DELIVERING IMPLANTS AND METHODS THEREOF", and U.S. application Ser. No. 13/598,143, filed on Aug. 29, 2012, entitled "A MULTI-ARM TOOL FOR DELIVERING IMPLANTS AND METHODS THEREOF". The entirety of each of these related applications is incorporated by reference herein.

TECHNICAL FIELD

The invention relates to devices and methods for delivering one or more implants into the body of a patient such as a human or an animal.

BACKGROUND

Urinary incontinence, or loss of bladder control, is a condition that causes people to involuntarily leak urine while coughing, sneezing, laughing, and exercising. Men and women both suffer from incontinence. Almost 16 percent of the women population suffers from urinary incontinence, and men account for a quarter the total patient population.

Typically, urinary incontinence is treated by placing a supportive implant, often called a sling, into the pelvic region of a patient. The supportive implant is used to cradle or support the bladder or urethra, depending on the procedure. Supportive implants are delivered to the pelvic region through one or more vaginal incisions and/or through exterior incisions in body of the patient. In addition to urinary incontinence, supportive implants placed into the pelvic region can also be used to correct various pelvic prolapse conditions, which include uterine prolapse, rectocele, cystocele, and urethrocele.

The common procedure for delivering such implants into the pelvic region of the patient involves a delivery tool that has a long curved shaft with a hooked needle tip attached to a handle. A surgeon maneuvers by hand the delivery tool into and within the pelvic region through and/or around tissue where the implant is desired to be placed. Once positioned, the surgeon must further manipulate the delivery tool by hand to capture an implant attached to a looped end onto the hooked needle tip. In some instances, the surgeon may require an additional tool to grasp the implant and place the implant onto the hooked needle tip. After which, the surgeon withdraws the delivery tool to position the implant in the desired location.

The above procedure is limited because it requires direct vision of the surgeon to capture the implant in the difficult to access regions of the pelvic. In addition, the delivery tool is hard to control by hand, and often the delivery tool deviates from the desired path of implantation. This deviation can result in failed attempts to capture the implant and to improper placement of the implant. Moreover, deviation of the delivery tool can result in inadvertent tissue, nerve, bladder, or urethral damage, and any required additional attempts at implant delivery significantly increase the risk of such tissue and/or nerve damage.

SUMMARY

Devices and methods of the invention allow an operator to deliver and position an implant into the body of a patient without the need for direct-vision of the operator or the need to handguide a needle in order to capture an implant. Because the delivery device does not require the operator to hand guide the needle, the device significantly lessens inadvertent tissue damage caused by needle deviation. In addition, the delivery device advantageously allows one to pre-position the implant into the body. Once pre-positioned, the device guides the needle through a desired implantation location directly to the implant for capture, and then the needle pulls the captured implant to the desired location. This diminishes the risk of improper placement of the implant and increases successful capture events.

A medical device according to the invention can include a needle receiving arm with at least a portion that is curved. The needle receiving arm is configured to hold an end portion of an implant at its distal portion. The end portion of the implant can include a suture. The suture can be fixedly attached or otherwise coupled to an end of the implant, and the implant can be designed for placement into a pelvic region of a female human patient to raise the bladder neck and thus treat female urinary incontinence. Alternatively, the implant may be used to correct various pelvic prolapse conditions, which include uterine prolapse, rectocele, cystocele, and urethrocele. The distal portion of the needle receiving arm includes an opening that leads to a cavity for receiving a needle. The cavity includes inner walls that are angled to direct the needle when the needle advances towards the cavity through the opening. The angled walls facilitate movement of the needle into a position within the cavity where the implant end gets engaged with the needle such as in one or more slots defined on a distal portion of the needle. This medical device also includes a clamping arm that is movably coupled to the receiving arm via a junction section, and the clamping arm also is curved along at least a portion of its length. The clamping arm includes a needle deployment mechanism for advancing the needle towards the cavity of the receiving arm. The needle deployment mechanism is configured for both advancing the needle and also retracting the needle out of the cavity and back through the tissue. The retracting needle pulls the implant end with it as it pulls back out of the cavity and back through the tissue.

An operator of this medical device uses the needle deployment mechanism to advance the needle through tissue of a patient and toward the cavity of the needle receiving arm, where the angled walls of the cavity direct the advancing needle into a position where the needle's slot is able to engage with the implant end that is held. The angled walls can be provided on a top surface as well as on the sides of the cavity. The top walls align and direct the tip of the needle while it advances within the cavity. The side walls align the needle along its sides and push the needle to the correct location within the cavity. The walls and their slopes are designed to cause the advancing needle to engage reliably and repeatedly with the implant end portion or suture coupled to the implant without the operator having to aim the needle or otherwise take any steps other than deploy the needle using the device's needle deployment mechanism.

In one aspect, the invention relates to a medical device for delivering one or more implants into the body of a patient. The device comprises a first portion and a second portion. The first portion comprises a handle, a junction section extending distally from the handle, and a needle-receiving arm extending distally from the junction section. At least a portion of the needle-receiving arm is curved. The needle-receiving arm comprises a distal portion configured to releasably hold an end portion of an implant. The distal portion defines an end opening leading to a cavity for receiving a needle comprising a retaining slot. The cavity comprises at least two inner walls angled to direct the needle when the needle is advanced through the end opening and into the cavity and into a position where the releasably-held implant end portion is disposed in the retaining slot of the needle. The second portion of the medical device comprises a clamping arm movably coupled to the junction section to allow an operator of the medical device to hold the handle and manually move the clamping arm with respect to the first portion. At least a portion of the clamping arm is curved. The clamping arm comprises a needle deployment mechanism for advancing the needle through tissue of the body of the patient and into the cavity of the distal portion of the needle-receiving arm to allow the releasably-held implant end portion to be disposed in the retaining slot of the advanced needle. The needle deployment mechanism of the clamping arm also retracts the advanced needle out of the cavity and back through the tissue to pull the end portion of the implant (that is disposed in the retaining slot of the needle) back through the tissue.

Embodiments according to this aspect of the invention can include various features. For example, the end portion of the implant can be a suture with a loop that is releasably held by the distal portion of the needle-receiving arm, and the suture can extend from one end of the implant. The suture can extend from that end of the implant by being fixedly attached to that end of the implant or otherwise coupled to that end of the implant. The suture can extend from one end of a packaging in which the implant is contained. The suture can be formed of metal, biological material, and/or synthetic material. The implant can be a sling configured, for example, for implantation into the body of the patient to treat female urinary incontinence by raising or supporting the patient's bladder neck. The needle deployment mechanism of the clamping arm can have a distal portion and a proximal portion, and it can comprise a sliding component and a curved guide rail, where the sliding component is coupled to the needle such that movement of the sliding component translates into movement of the needle, and where the sliding component is movably coupled to the curved guide rail to allow the operator to manually move the sliding component distally along the curved guide rail to advance the needle and to manually move the sliding component proximally along the curved guide rail to retract the needle. This sliding component can comprise a grasping element for manually moving the sliding component along the curved guide rail, and the grasping element can be coupled to a syringe operably associated with the needle. And the clamping arm can further comprise a guide compartment located distal to the needle deployment mechanism, where the guide compartment comprises a lumen through which the needle passes as the needle is advanced and retracted, and where the guide compartment assists in biasing the advancing needle towards the cavity. The movement of the sliding component can be independent from the movement of the clamping arm.

The at least two angled walls can comprise a first wall and second wall angled to slideably direct the needle into a position so that the retaining slot of the needle is beneath the implant end portion when the needle passes the first and second angled walls, and the needle can be configured to spring up towards the implant end portion upon passing the first and second angled walls to dispose the implant end portion into the retaining slot of the needle. The distal portion of the receiving arm can further comprise at least one slit for releasably holding the implant end portion in the cavity, and the implant end portion can be held across the cavity and substantially perpendicular to the advanced needle. And the needle can comprise a beveled tip configured to align with the angle of at least one of the at least two walls. In another embodiment, the first wall further includes a recess configured to force the needle to spring upward, as the needle retracts, to further push the implant end portion into the retaining slot of the needle. In yet another embodiment, the at least two inner walls further include at least one side wall configured to further slideably direct the needle into the cavity such that the needle slides against the implant end portion. In some embodiments, the at least two inner angled walls form a funnel-like structure configured to direct the needle to a specific portion of the cavity.

In another aspect, the invention relates to a medical device for delivering one or more implants into the body of a patient. This device again comprises a first portion and a second portion, but the first portion does not necessarily include a handle and instead comprises at least a junction section and a needle-receiving arm extending distally from the junction section. At least a portion of the needle-receiving arm is curved, and the needle-receiving arm comprises a distal portion configured to releasably hold an end portion of an implant. The distal portion defines an end opening leading to a cavity for receiving a needle comprising a retaining slot. The cavity comprises a first cavity portion and a second cavity portion, where the first cavity portion defines a lumen through which a part of the implant end portion is exposed to the needle for capture, and where the second cavity portion comprises at least two inner walls angled to direct the needle when the needle is advanced through the end opening and into the cavity towards the first cavity portion and into a position where the exposed implant end portion is captured in the retaining slot of the needle. The second portion of the medical device comprises a clamping arm movably coupled to the junction section to allow an operator of the medical device to manually move the clamping arm with respect to the first portion. At least a portion of the clamping arm is curved, and the clamping arm comprises a needle deployment mechanism and a guide compartment distal to the needle deployment mechanism. The guide compartment has a longitudinal axis and defines a lumen through which the needle passes as the needle is advanced and retracted, and the guide compartment is configured for biasing the needle towards the cavity portion. The needle deployment mechanism is for advancing the needle into the guide compartment, through tissue, and into the cavity of the distal portion of the needle-receiving arm to allow the exposed releasably-held implant end portion to be captured in the retaining slot of the advanced needle. The needle deployment mechanism of the clamping arm also is for retracting the advanced needle and the captured implant end portion out of the cavity and through the tissue.

Embodiments according to this other aspect of the invention also can include various features. For example, the end portion of the implant can be a suture with a loop that is releasably held by the distal portion of the needle-receiving arm. The suture can extend from one end of the implant. The suture can extend from one end of a packaging in which the implant is contained. The implant can be a sling configured for implantation into the body of the patient to treat female urinary incontinence by raising or supporting the patient's bladder neck. The needle deployment mechanism of the clamping arm can have a distal portion and a proximal portion and can comprise a sliding component and a curved guide rail. The sliding component can be coupled to the needle such that movement of the sliding component translates into movement of the needle, and the sliding component can be movably coupled to the curved guide rail to allow the operator to manually move the sliding component distally along the curved guide rail to advance the needle and to manually move the sliding component proximally along the curved guide rail to retract the needle. The sliding component can comprise a grasping element for manually moving the sliding component along the curved guide rail, and the grasping element can be coupled to a syringe operably associated with the needle. Movement of the sliding component can be independent from movement of the clamping arm. The distal portion of the needle receiving arm can include at least two angled walls. The at least two angled walls can comprise a first wall and second wall angled to slideably direct the needle into a position so that the retaining slot of the needle is beneath the exposed implant end portion when the needle passes the first and second angled walls, and the needle can be configured to spring up towards the implant end portion for capture upon passing the first and second angled walls. The distal portion of the receiving arm can further comprise at least one slit for releasably holding the implant end portion in the cavity and the implant end portion can be held across the cavity and substantially perpendicular to the advanced needle. And the needle can comprise a beveled tip configured to align with the angle of at least one of the at least two walls. In another embodiment, the first wall further includes a recess configured to force the needle to spring upward, as the needle retracts, to further push the implant end portion into the retaining slot of the needle. In yet another embodiment, the at least two inner walls further include at least one side wall configured to further slideably direct the needle into the cavity such that the needle slides against the implant end portion. In some embodiments, the at least two inner angled walls form a funnel-like structure configured to direct the needle to a specific portion of the cavity.

In another aspect of the invention, the medical device includes a first portion and a second portion. The first portion includes needle receiving arm and the second portion includes a clamping arm. The clamping arm and needle receiving arm may be movably coupled with respect to each other. The clamping arm may include a needle deployment mechanism to deploy a needle through tissue and into a distal portion of the needle-receiving arm to capture an end portion of an implant. The needle includes a retaining slot for capturing the end portion of the implant. The distal portion of the receiving arm is configured to releasably hold the end portion of an implant. In addition, the distal portion defines an end opening leading to a cavity for receiving the needle. The cavity can include at least two inner angled walls. In one embodiment, the at least two inner angled walls includes a first wall that directs the needle into a position so that the needle slides against the implant end portion until the implant end portion enters the retaining slot of the needle. The implant end portion can be releasably-held against a portion of the first wall. The first wall may be angled to position the needle beneath the releasably-held implant end portion as the needle advances into the cavity. The first wall may further include a recess configured to force the needle to spring upward, as the needle retracts, to position the implant end portion further into the retaining slot of the needle. The at least two inner walls may further include at least one side wall configured to further direct the needle, as the needle advances, against the implant end portion. In one embodiment, the at least two inner angled walls form a funnel-like structure to direct the needle, as the needle advances, against and beneath the implant end portion disposed within the cavity.

Other objectives, aspects, features, details, and advantages according to the invention will become apparent from the following description when read in conjunction with and with reference to the drawings.

DESCRIPTION

The terms proximal and distal as used herein refer to a perspective of an operator. The operator may be a surgeon, a physician, a nurse, a doctor, a technician, or other human operator who may perform the methods or operations described herein. The term proximal refers to an area or a direction that is near or closest to the operator, and the term distal refers to an area or direction that is away from the operator. The patient referred to herein can be a human or any other animal and can be a male or a female.

The devices described herein may be inserted into and/or used in conjunction with various medical procedures on a patient's pelvic region or another area of the patient. The devices and methods described herein can be used to deploy an implant into the pelvic region of a patient to treat one or more pelvic dysfunctions. For example, the implant can be used to treat urinary incontinence in a human female patient by raising the bladder neck of the patient.

The disclosed devices may be used to place one or more implants through a vaginal incision, in a retro-pubic direction (behind the pubic bone) or in a pre-pubic direction (in front of the pubic bone). In other embodiments, the implant can be placed to target other anatomical structures or tissues as desired.

Detailed embodiments according to the present invention are disclosed herein. It is to be understood, however, that the disclosed embodiments are merely exemplary and are not to be interpreted as limiting.

Figure 1A:
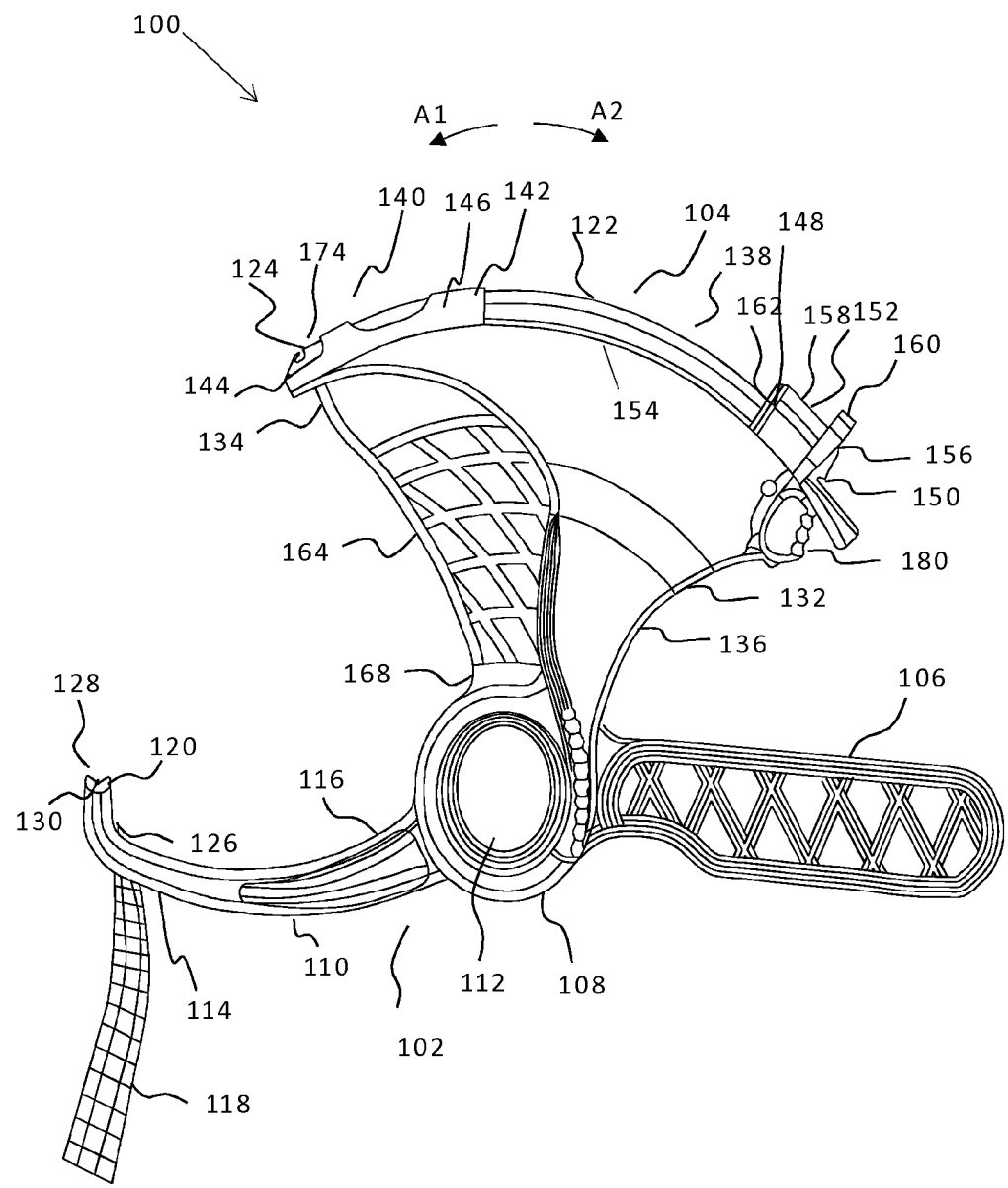
FIG. 1A illustrates a side view of a medical device in an open configuration.

FIG. 1A is a perspective view of a medical device 100 in an open configuration. The medical device 100 is configured to be used as an insertion tool or delivery tool for an implant 118 to be placed into a patient's body (e.g., a female patient, a male patient, etc.). The medical device 100 can be used for placing an implant 118 within a tissue of the patient's body. The implant 118 can be coupled to a suture 126, which can be releasably held by the medical device 100. The medical device 100 can facilitate placement of the suture, thereby facilitating placement of the implant 118 into the patient's body. In some embodiments, the medical device 100 is configured to be used to insert the implant 118 into a patient's body using an outside-in approach (e.g., an outside-in approach via a vaginal incision in the patient's body or an outside-in approach via a rectal incision in the patient's body). In some embodiments, the medical device 100 can be configured to place the implant 118 into a pelvic region of a patient. Specifically, in some embodiments, the medical device 100 is configured to place the implant 118 through an obturator muscle and/or a membrane of a patient.

The medical device 100 includes a first portion 102 and a second portion 104. The first portion 102 includes a handle 106, a junction section 108 extending distally from the handle 106, and a needle-receiving arm 110 extending distally from the junction section 108. The handle 106 is configured to provide a means to hold the medical device 100. The junction section 108 can be configured to include a finger hole 112. The needle-receiving arm 110 can be straight, curved, or a combination of both. In an embodiment, at least a portion of the needle-receiving arm 110 has a curved profile. The needle-receiving arm 110 includes a distal portion 114 and a proximal portion 116. The distal portion 114 can be configured to releasably hold an end portion of the implant 118. The distal portion 114 defines an end opening 128 leading to a cavity 120 for receiving a needle 122 having a retaining slot 124. The distal portion 114 can include a slit 130 for housing the suture 126 or at least a portion of the implant 118. The cavity 120 can be configured to releasably hold the end portion of the implant 118. The cavity 120 is configured to receive at least a part of the implant 118 or a suture 126 (FIGS. 6-10 describe some exemplary implants that can be placed using the medical device 100).

In some embodiments, the end portion of the implant 118 is a looped structure (illustrated in FIG. 8) that is releasably held by the distal portion 114 of the needle-receiving arm 110. In some embodiments, the suture 126 can be coupled to a portion of the implant 118 (illustrated in FIGS. 9A and 10). In some embodiments, the suture 126 extends from one end of the implant 118. In some embodiments, the suture 126 extends from one end of a packaging, including but not limited to a sheath or a sleeve, in which the implant 118 is contained. In some embodiments, the suture 126 comprises a material selected from the group consisting of a metal, a biological material, and a synthetic material. In some embodiments, the implant 118 is a sling configured for implantation into the patient's body to treat female urinary incontinence by raising or supporting the patient's bladder neck.

The second portion 104 of the medical device 100 includes a clamping arm 132 movably coupled to the junction section 108 to allow an operator of the medical device 100 to hold the handle 106 and manually move the clamping arm 132 with respect to the first portion 102. The clamping arm 132 of the medical device 100 is configured to be movable with respect to the needle-receiving arm 110. The clamping arm 132 includes a distal portion 134 and a proximal portion 136. The clamping arm 132 can be straight, curved, or a combination of both. In an embodiment, at least a portion of the clamping arm 132 is configured to have a curved profile. The clamping arm 132 includes a needle deployment mechanism 138 and a guide compartment 140. The guide compartment 140 includes a proximal portion 142, a distal portion 144, and a lumen 146 extending from the proximal portion 142 to the distal portion 144. The guide compartment 140 can dispose at least a portion of the needle 122 into the lumen 146. The needle 122 passes through the lumen 146 and is adapted to advance out of the lumen 146 and can also be retracted within the lumen 146. The guide compartment 140 assists in biasing the advancing needle 122 towards the cavity 120. The guide compartment 140 can be placed at the distal portion 134 of the clamping arm 132. The needle 122 is connected to the needle deployment mechanism 138 of the clamping arm 132. The guide compartment 140 can be configured to support the movement of the needle 122. The needle 122 can be at least partially disposed into the guide compartment 140 of the clamping arm 132. The needle 122 is configured to at least partially exit the guide compartment 140 or the lumen 146 in the deployed state and may be completely contained inside the guide compartment 140 or lumen 146 in the retracted state of the suturing device 100. The guide compartment 140 can be configured to support the movement of the clamping arm 132 towards the needle-receiving arm 110 to engage the suture 126 or a distal end of the implant 118 (described later).

The needle deployment mechanism 138 has a distal portion 148 and a proximal portion 150. The needle deployment mechanism 138 includes a sliding component 152 and a guide rail 154. The sliding component 152 includes a proximal portion 156 and a distal portion 158. The sliding component can be placed at the proximal portion 136 of the clamping arm 132. The sliding component 152 can include a grasping element 160 coupled to the proximal portion 156 of the sliding component 152. The distal portion 158 of the sliding component 152 can include an opening 162 in which a portion of the needle 122 is disposed, or the needle 122 can be affixed to the sliding component 152. In one embodiment, the needle 122 is removably disposed within the opening 162 of the sliding component 152. The grasping element 160 can facilitate manual movement of the sliding component 152 along the guide rail 154. The sliding component 152 is coupled to the needle 122 such that movement of the sliding component 152 translates into movement of the needle 122. In some embodiments, the guide rail 154 can follow a curved profile. The sliding component 152 can be movably coupled to the guide rail 154 to allow the operator to manually move the sliding component 152 distally along the guide rail 154 to advance the needle 122 and to manually move the sliding component 152 proximally along the curved guide rail 154 to retract the needle 122. The sliding component 152 is independent from the movement of the clamping arm 132. In some embodiments, the needle deployment mechanism 138 can include at least one of a piston, a spring, an actuator, and the like mechanism to make the sliding component 152 movable. In an embodiment, the needle deployment mechanism 138 can be configured to include a locking mechanism. The locking mechanism can lock the sliding component 152 and the needle 122 at a desired location. The needle deployment mechanism 138 can facilitate advancement of the needle 122 through tissue of the patient's body by facilitating the sliding movement of the needle 122 from the second portion 104 to the first portion 102 of the medical device 100. The needle deployment mechanism 138 can be configured for advancing the needle 122 through the tissue of the patient's body and into the cavity 120 of the distal portion 114 of the needle-receiving arm 110 to allow the releasably-held implant 118 end portion to be disposed in the retaining slot of the advanced needle 122. The needle deployment mechanism 138 of the clamping arm 132 also facilitates retracting the advanced needle 122 out of the cavity 120 and back through the tissue to pull the end portion of the implant 118 that is disposed in the retaining slot of the needle 122. The sliding component 152 can be coupled to the needle 122 such that the movement of the sliding component 152 translates into the movement of the needle 122. The sliding component 152 can be movably coupled to the curved guide rail 154, which can allow the operator to manually move the sliding component 152 distally along the curved guide rail 154 to advance the needle 122. The operator can also manually move the sliding component 152 proximally along the curved guide rail 154 to retract the needle 122.

Figure 1B:
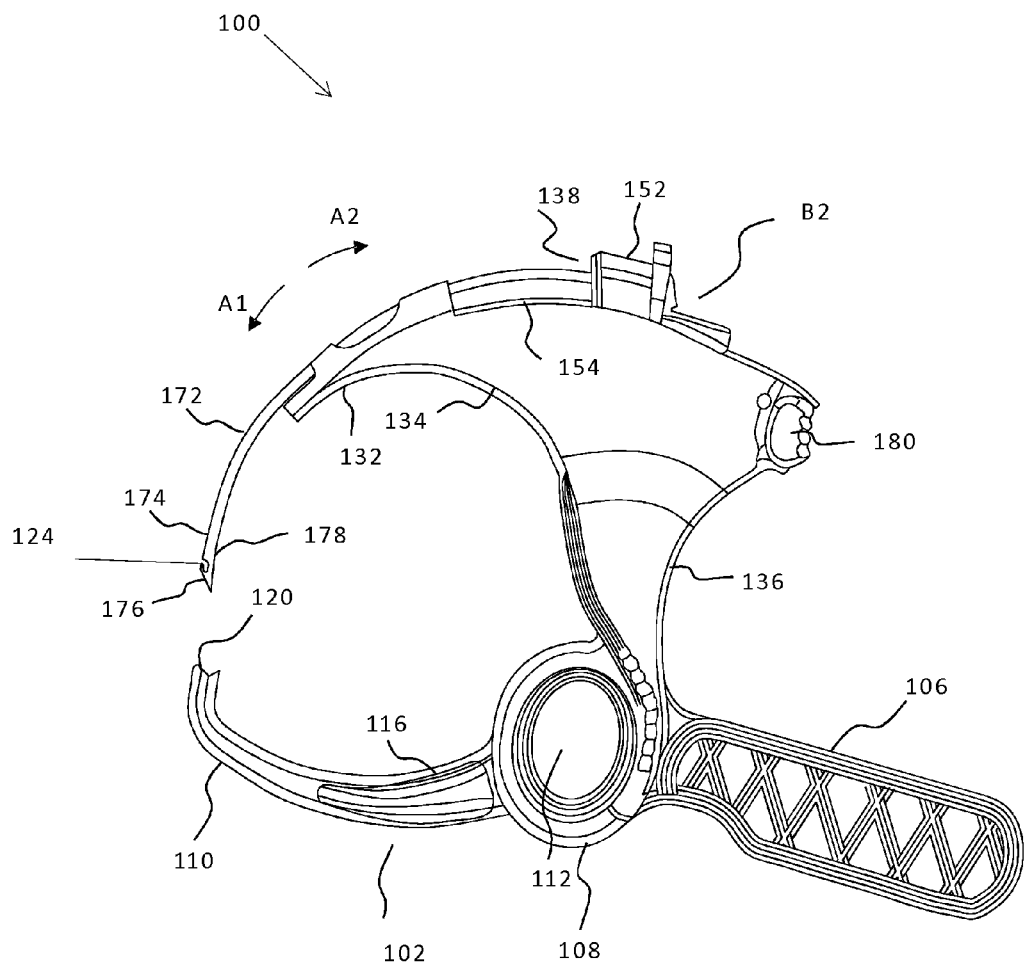
FIG. 1B illustrates a side view of the medical device in a partially closed position.
Figure 1C:
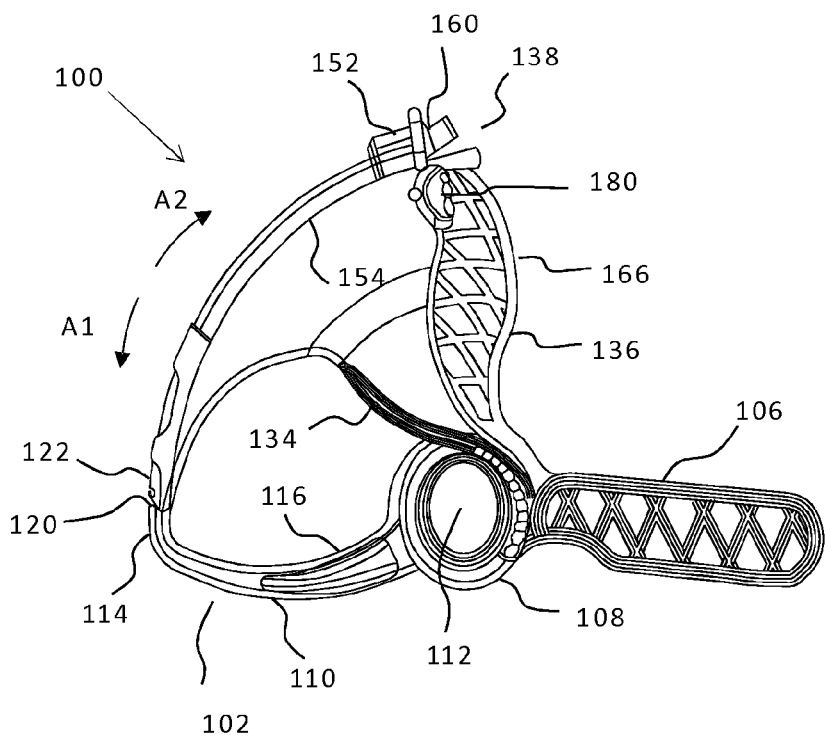
FIG. 1C illustrates a side view of the medical device in a closed position.
Figure 1D:
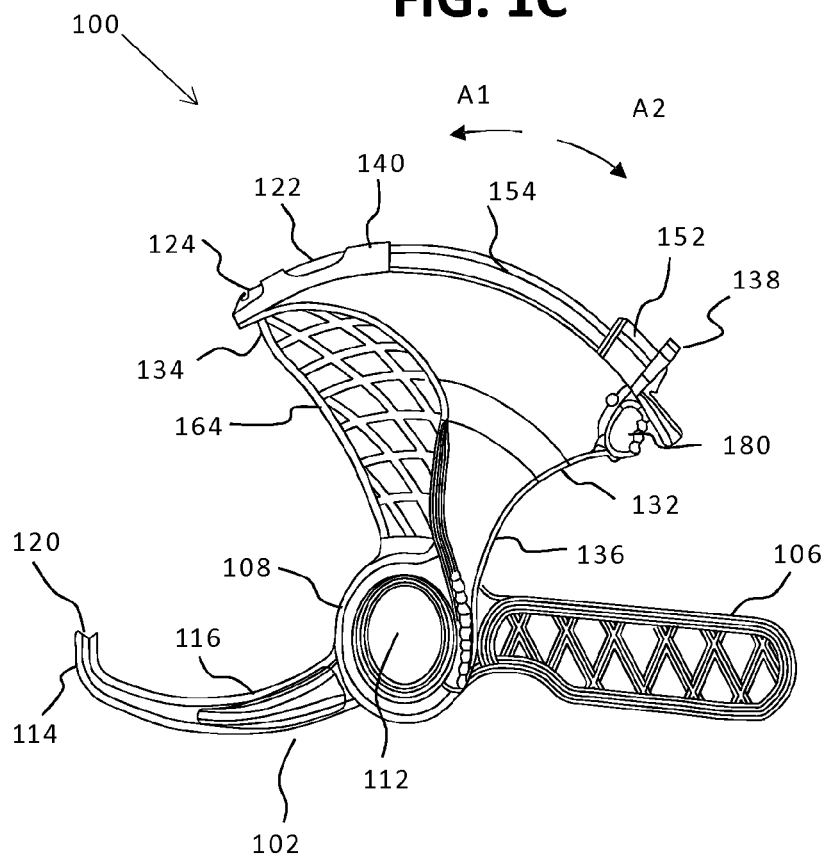
FIG. 1D illustrates the medical device in an open position.

In one aspect, the medical device includes an inner guide 164 which can be disposed within the clamping arm 132. The inner guide 164 includes a proximal portion 166 and a distal portion 168. The clamping arm 132 is slideably disposed over the inner guide 164, and the inner guide 164 facilitates the sliding movement of the clamping arm 132 towards the needle-receiving arm 110. FIGS. 1A and 1D shows the distal portion 168 of the inner guide 164 exposed with the clamping arm 132 in an open configuration. FIG. 1B shows the inner guide 164 completely disposed within the clamping arm 132, which is in a partially closed position. FIG. 1C shows the proximal portion 166 of the inner guide 164 exposed with the clamping arm 132 in a closed position.

The needle 122 includes a proximal portion 172 (illustrated in FIG. 1B) and a distal portion 174 (illustrated in FIG. 1B). At least a portion of the needle 122 is disposed in the lumen 146 of the guide compartment 140 (See FIGS. 1A-1D). The distal portion 174 of the needle 122 includes the retaining slot 124 (illustrated in FIGS. 1A and 1B) and a tip portion 178 (illustrated in FIG. 1B) with a beveled edge 176 (details of needle explained later in FIGS. 3A-3B).

Referring to FIGS. 1B-1D in conjunction with FIG. 1A, the procedure of operation of the medical device 100 is described. FIG. 1B illustrates a side view of the medical device 100 in a partially closed configuration. FIG. 1C illustrates a side view of the medical device 100 in a closed position. FIG. 1D illustrates the medical device 100 again in an open position. Therefore, FIGS. 1A-1D illustrate the entire cyclic positions of the medical device 100, i.e., from open to closed and further back to open positions.

The proximal portion 136 (illustrated in FIG. 1A) of the clamping arm 132 (illustrated in FIG. 1A) is attached to the proximal portion 116 of the needle-receiving arm 110 via the junction section 108 of the medical device 100. The clamping arm 132 can be coupled to the needle-receiving arm 110 such that the clamping arm 132 is free to move towards the needle-receiving arm 110. The clamping arm 132 can be configured to be movably coupled to the needle-receiving arm 110. For example, the clamping arm 132 can be configured to be at least rotatably coupled, slidably coupled, or hingedly coupled to the needle-receiving arm 110. In some embodiments, the clamping arm 132 and the needle-receiving arm 110 are connected to the junction section 108 via fasteners, such as a screw or a pin. The clamping arm 132 can be movably coupled to the junction section 108 to allow an operator of the medical device 100 to hold the handle 106 and manually move the clamping arm 132 with respect to the first portion 102.

The medical device 100 can be used by a physician to place the implant 118 within the patient's body. After the implant 118 is releasably placed in the cavity 120 of the needle-receiving arm 110, the receiving arm 110 of the medical device 100 is externally inserted in the patient's body by the physician. For example, the medical device 100 may be inserted into the patient's body to an implant site such as the pelvic region by the physician. The medical device 100 may be inserted through the vaginal opening to place the implant 118 in the pelvic region. The medical device 100 can be configured to be held via the handle 106 and gripped using the finger hole 112 by the physician.

Once the medical device 100 is inserted inside the body, the physician applies a force via the push tab 180. The force applied on the push tab 180 moves the clamping arm 132 towards the receiving arm 110 to clamp against tissue disposed between the receiving arm and the clamping arm. The operator can then distally deploy the needle 122 through the tissue by moving the sliding component 152 by pushing the grasping element 160. The sliding component 152 slideably moves along the guide rail 154. The movement of the sliding component 152 allows the needle 122 to move in a direction A1 towards the needle-receiving arm 110. In some embodiments, pulling on the grasping element 160 can cause movement of the needle 122 in a direction A2. The needle can also be moved out of the tissue by grabbing the push tab 180, which moves the clamping arm 132 away from the receiving arm 110. In some aspects, medical device 100 can include a locking element on the clamping arm 132 that locks the clamping arm in a specific position. The clamping arm 132 of the medical device 100 can be configured to be fixed at any location along the direction A1 by the locking mechanism.

The suture can be held by the cavity 120 of the needle-receiving arm 110. The cavity 120 can be designed to engage the suture 126 blindly with the needle 122. Specifically, the needle 122 can be configured to enter into the cavity 120 of the needle-receiving arm 110 to engage the suture 126 without any external aid to view the engagement.

The guide rail 154 provides a guide path for the needle 122 and the sliding component 152. As the sliding component 152 slides over the guide rail 154, the needle 122 moves towards the needle-receiving arm 110. As the needle 122 moves along the guide rail 154, the distal portion 174 of the needle 122 advances out of the guide component 164. The guide component 164 can be configured to provide stability to the needle 122 while moving along the guide rail 154. The guide component 164 can be configured to guide the needle 122 towards the cavity 120 of the needle-receiving arm 110.

In an embodiment, the medical device 100, can be made of ultra violet (UV) cured epoxy resin. In some embodiments, the UV cured epoxy resin can be fabricated by Stereo Lithography Apparatus (SLA). In some embodiments, various components of the medical device 100 can be made of any plastic or metal (such as polycarbonate or 304 stainless steel) materials. Other embodiments may include use of manufacturing methods including but not limited to molding or machining components and materials including but not limited to metals, polymers and ceramics.

Figure 2A:
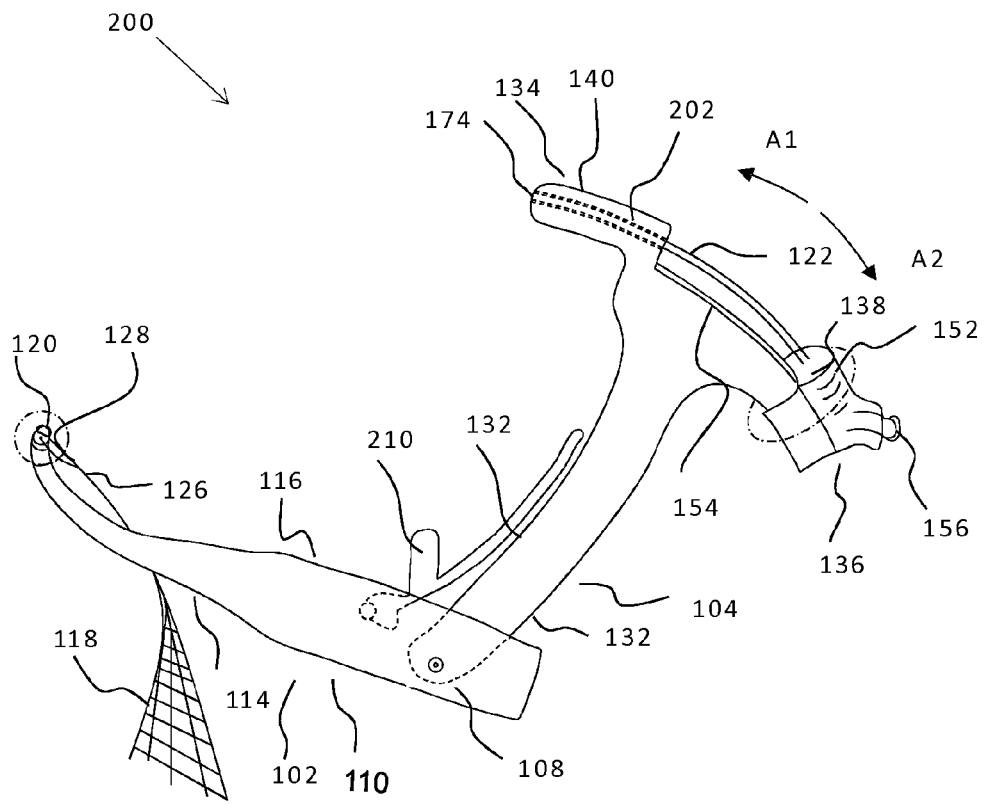
FIG. 2A is a side view of a medical device in an open configuration, according to an embodiment of the invention.

FIG. 2A is a side view of a medical device 200, in an open configuration, according to another embodiment of the present disclosure. The medical device 200 can be configured to be used as an insertion tool, and/or a delivery tool to place an implant 118 in the patient's body. The medical device 200 can include a first portion and a second portion that are structurally and functionally similar to the first portion 102 and the second portion 104 of the medical device 100. The medical device 200 may not include the handle 106. The medical device 200 can include a locking mechanism 210 to lock in place the clamping arm with respect to the needle receiving arm. Locking mechanism 210 may comprise a ratchet mechanism.

The second portion 104 of the medical device 200 can be configured to include the clamping arm 132. The clamping arm 132 can include a guide compartment 130 defining a lumen 202 at the distal portion. The clamping arm 132 also includes a needle deployment mechanism which can have a guide rail 154 and a sliding component 138. The needle deployment extends from a proximal portion 136 and a distal portion 134 on a cross-section portion of the clamping arm. In an embodiment, at least a portion of the clamping arm 132 is configured to have the curved profile. For example, the portion of the clamping arm having the needle deployment mechanism can be curved. The clamping arm 132 can be configured to include the needle 122. The needle 122 can extend from the distal portion 134 to the proximal portion 136 of needle deployment mechanism. The distal portion 174 of the needle 122 can be configured to be housed within the lumen 202. The distal portion 174 can include the beveled edge 176. The beveled edge 176 can be configured to engage with the suture 126. The proximal portion 172 of the needle 122 can be attached to the sliding component 152. The sliding component 152 can be configured to slide over the guide rail 154. The guide rail 154 provides the path for the sliding component 152 to slide from the proximal portion 136 to the distal portion 134 of needle deployment mechanism of the clamping arm 132. The guide rail 154 provides a path for the needle 122 to travel towards the needle-receiving arm 110 via the needle deployment mechanism 138. A proximal portion 133 of the clamping arm 132 and the proximal portion 116 of the needle-receiving arm 110 can be attached via the junction section 108. In an embodiment, the clamping arm 132 can be configured to be at least rotatably coupled, or slidably coupled or hingedly coupled to the needle-receiving arm 110. In some embodiments, the clamping arm can be configured to move towards the needle-receiving arm 110. In an embodiment, the clamping arm 132 can be movably coupled to the junction section 108 to allow an operator of the medical device 200 to manually move the clamping arm 132 with respect to the first portion 102. In an embodiment, the operator can manually move the needle 122 by applying a force on the sliding component 152. The sliding component 152 can be configured to slide over the guide rail 154 to enter the cavity 120 of the needle-receiving arm 110. In an embodiment, the cavity 120 of the distal portion 114 of the needle-receiving arm 110 can be configured to allow the releasably-held end portion of the implant 118 to be disposed in the retaining slot 124 of the advanced needle 122. The clamping arm 132 includes the needle deployment mechanism 138 for retracting the advanced needle 122 out of the cavity 120 back through the tissue to pull the end portion of the implant 118.

Figure 2B:
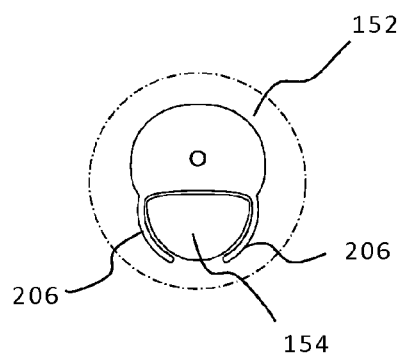
FIG. 2B is a cross-sectional view of a sliding component of the medical device.

FIG. 2B is a cross-sectional view of sliding component 152 slidably disposed on the guide rail of the needle deployment mechanism. The sliding component 152 of the clamping arm 132 is configured to be attached to the needle 122 so that the needle 122 can be moved along the guide rail 154. The sliding component 152 includes a plurality of sliding members 206 on both the sides. The sliding members 206 are configured to slide over the guide rail 154.

Figure 2C:
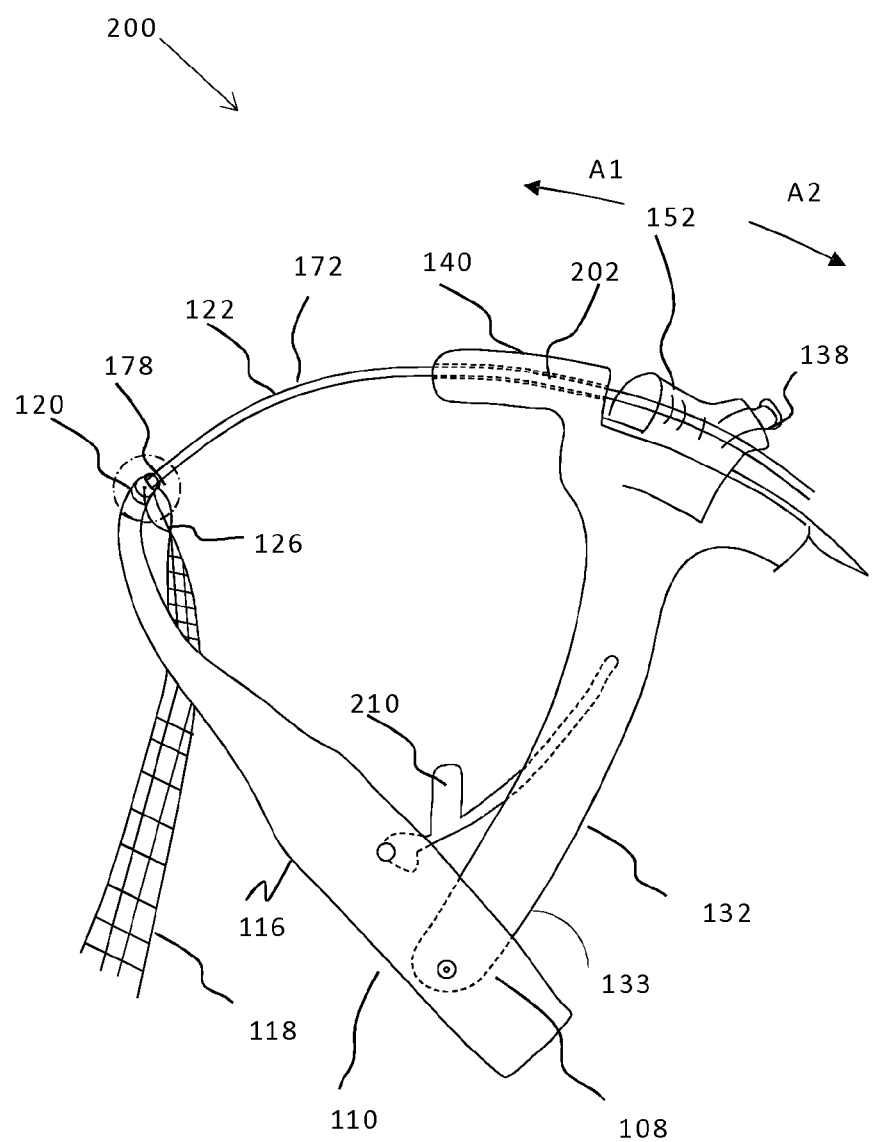
FIG. 2C is a side view of the medical device in a closed configuration.

FIG. 2C is a perspective view of the medical device 200 in a closed configuration. The sliding component 152 of the medical device 200 can be configured to move in a direction A1 on application of a force. The needle 122 can be configured to move in the direction A1 along with the movement of the sliding component 152. The tip portion 178 of the needle 122 advances out of the lumen 202 of the guide compartment 140 with the application of force. The guide compartment 140 can be configured to guide the needle 122 towards the cavity 120 of the needle-receiving arm 110. The guide compartment 140 can be configured to house the needle 122. Finally, the needle 122 enters the cavity 120 of the needle-receiving arm 110. The tip portion 178 of the needle 122 is configured to engage with the implant 118. The suture 126 placed in the cavity 120 of the needle-receiving arm 110 engages with the tip portion 178 of the needle 122. The suture 126 can be configured to carry the implant 118 to be placed in the patient's body.

Figure 2D:
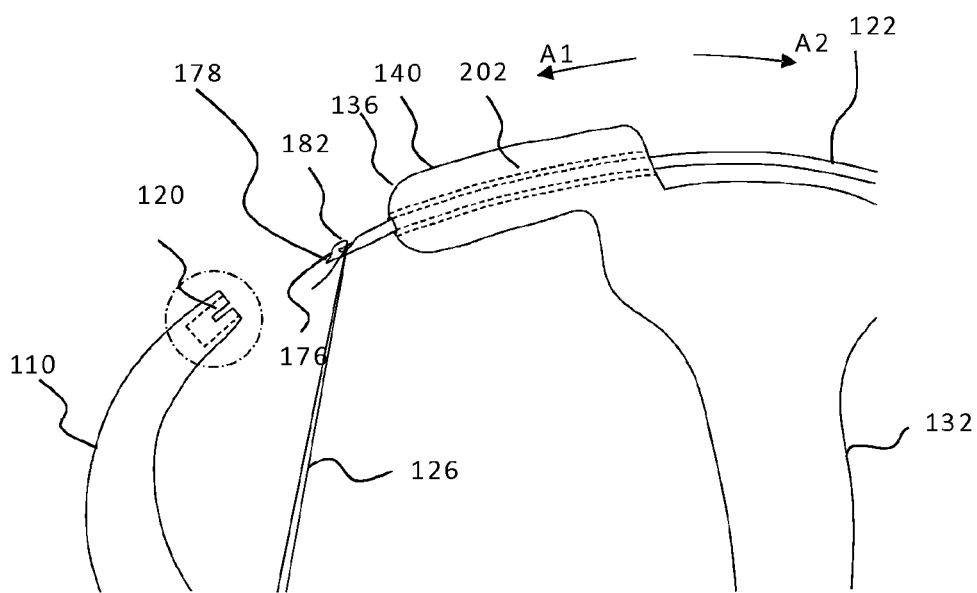
FIG. 2D is a side view of the medical device in an open position.

FIG. 2D is a side view of a portion of the medical device 200 in a retracted position with the suture 126 being carried by the needle 122. Once the suture 126 is engaged with the tip portion 178 of the needle 122, the needle 122 can be retracted. The sliding component 152 can be configured to move in the direction A2 for retraction. The movement of the sliding component 152 in the direction A2 can be configured to move the needle 122 in the direction A2. As the needle 122 is retracted from the cavity 120, the tip portion 178 of the needle 122 carries the suture 126 with it. The suture 126 coupled to the implant 118 is configured to travel along the needle 122 to the implant site. The medical device 200 is also configured to detach the implant 118 from the needle 122 and place the implant 118 at the implant site within the patient's body. As the implant 118 is placed inside the patient's body, the needle 122 can be completely retracted to its original position. In an embodiment, the medical device 200 can include a locking mechanism 210. The locking mechanism 210 can be configured to lock the clamping arm 132 and the needle-receiving arm 110 at any location along the direction of movement A1.

Figure 3A:
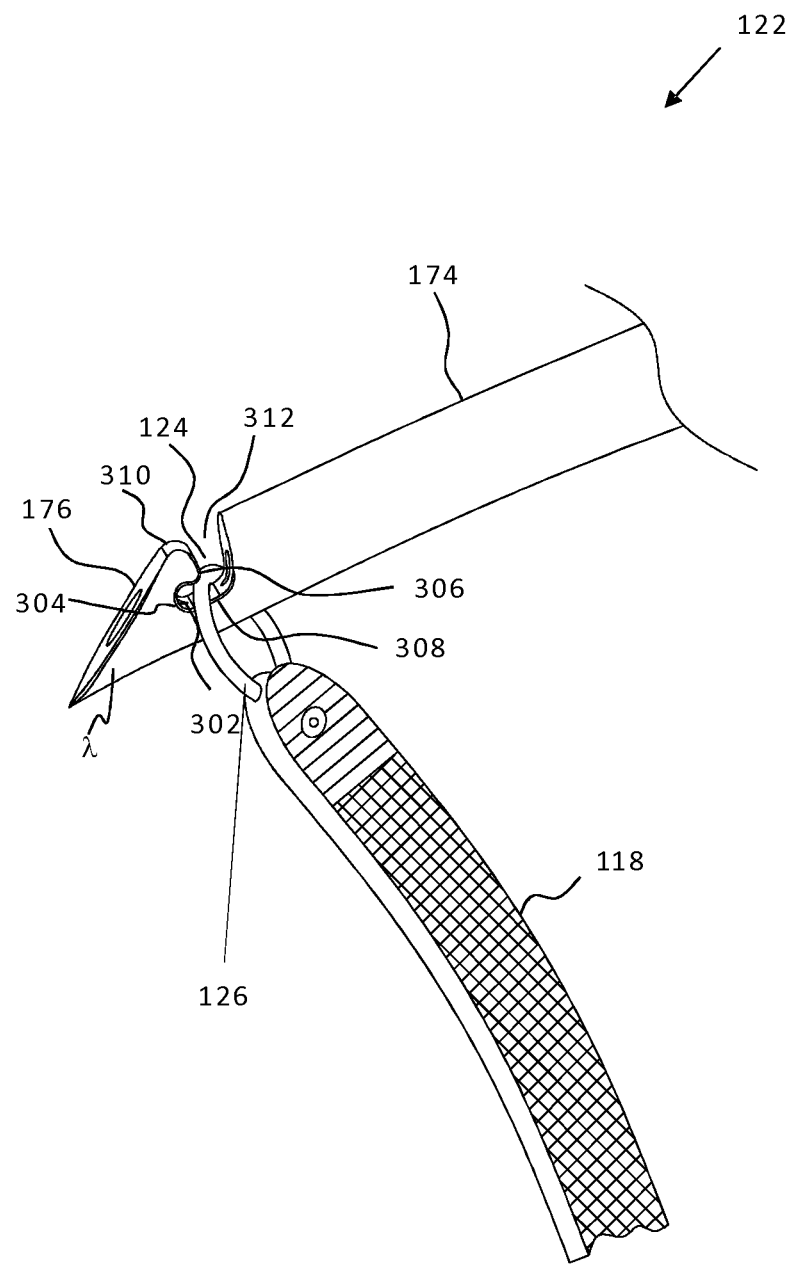
FIG. 3A is a perspective view of a distal portion of a needle of the medical device.

FIG. 3A illustrates a perspective view of the distal portion 174 of the needle 122 with the retaining slot 124 engaging the implant 118.

Figure 3B:
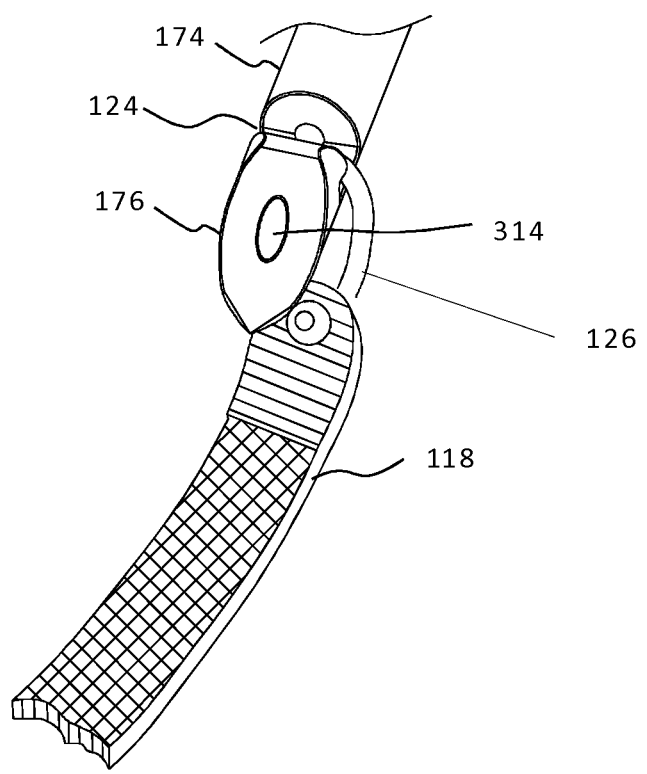
FIG. 3B is a perspective view of the distal portion of the needle with an implant inside a retaining slot of the needle.

FIG. 3B illustrates a perspective view of the retaining slot 124 and a portion of the implant 118 placed inside the retaining slot 124 in another view.

In some embodiments of the invention, the needle 122 can define a straight or curved profile. For example, the needle profile can be straight or curved to conform with the curvature or straightness of the needle deployment mechanism portion of the clamping arm. In some embodiments, the needle 122 has a substantially circular transverse cross section. In some embodiments, the transverse cross section of the needle 122 can be of a different shape other than a circular shape. For example, the cross-sectional shape (or outer shape) can be an elliptical shape or polygon shape, such as a square or a rectangular cross-sectional shape (or outer profile). In some embodiments, the needle 122 can have a tapered shape and/or a tapered portion (e.g., tapered from the proximal portion to the distal portion of the needle). In such embodiments, the needle 122 can have a varying diameter or width. In some embodiments, at least a portion of the needle 122 can be formed of a flexible material. For example, a portion of the needle 122 that remains disposed within the guide compartment 140 or the lumen 202 can be configured to flex or bend, when the medical device 100 or 200 is in the refracted state. In some embodiments, at least a portion of the needle 122 can be formed of the flexible material so that the portion of the needle 122 can conform to a curvature of the guide compartment 140 or lumen 146, as the needle 122 is slidably moved within the lumen 146. In an embodiment, a 0.072" needle 122 made of 17-4 stainless steel with Modulus of Elasticity $E=29\times10^6$ psi or any other stainless steel; mandrel or tubing, could be used. The retaining slot 124 of the needle 122 includes the beveled edge 176 (also referred to as needle bevel). The beveled edge 176 is defined by a bevel angle represented by $\lambda$. The dimension of the bevel angle $\lambda$ can vary based on the requirements. The beveled edge 176 can have a circular edge 310. In some embodiments, beveled edge 176 may include multiple facets or edges. The circular edge of the needle 122 abuts a pocket 302. The pocket 302 is defined by a wall 304, a floor 308 and a ceiling 306 of the retaining slot 124. The retaining slot 124 defines a suture opening 312. The beveled edge 176 can be configured to align with at least one of the two walls of the cavity 120 of the needle-receiving arm 110.

In certain embodiments, the needle is guided into the cavity 120 of the receiving arm 110 such that the suture 126 is placed within the retaining slot 124 of the needle 124. As the needle retracts, the needle 122 pulls the suture 126, and the implant coupled thereto, through the bodily tissue such that the implant is placed in a desired implant location within the tissue. The retaining slot 124 of the needle 122 is configured to pick up the suture 126 from the cavity 120 of the needle-receiving arm 110 in order to place the suture 126 through the bodily tissues. The beveled edge 176 of the needle 122 can be angled to align with the one or more of the angled walls of the cavity such that the needle slideably moves in the direction of the ramps 414, 416 when advanced forward into the cavity. This allows the needle 122 to be positioned so that the needle retaining slot is directly under the advanced needle when the needle is released into the open cavity. When the needle is released into the open cavity, the needle springs up, due to an upward bias, for example, and the suture is placed into the retaining slot for capture. The upward bias can be caused by the strength/flexibility of the needle that tend to force the needle upwards after being forced downward by the top ramp 414.

In one aspect, as the needle 122 is pushed through the bodily tissue and advances into the cavity 120, the structure of the cavity 120 directs the needle 122 such that the retaining slot 124 of the needle 122 is positioned beneath the suture 126 which is releasably placed across the cavity 120 of the needle-receiving arm 110. The cavity 120 is configured cause the needle to release and spring up towards the suture when the needle has advance so that the retaining slot is beneath the suture 126. This upward movement towards the suture allows the needle 122 to capture the suture 126 into the retaining slot 124. In one aspect, the suture 126 is placed onto the floor 308 of the retaining slot 124, and the wall 304 of the pocket 302 holds the suture 126 in place.

In some embodiments, the beveled edge 176 includes an opening extending from the beveled edge 176 to the retaining slot 124 of the needle 122.

FIGS. 4A-4E are perspective views of the distal portion 114 of the needle-receiving arm 110.

Figure 4A:
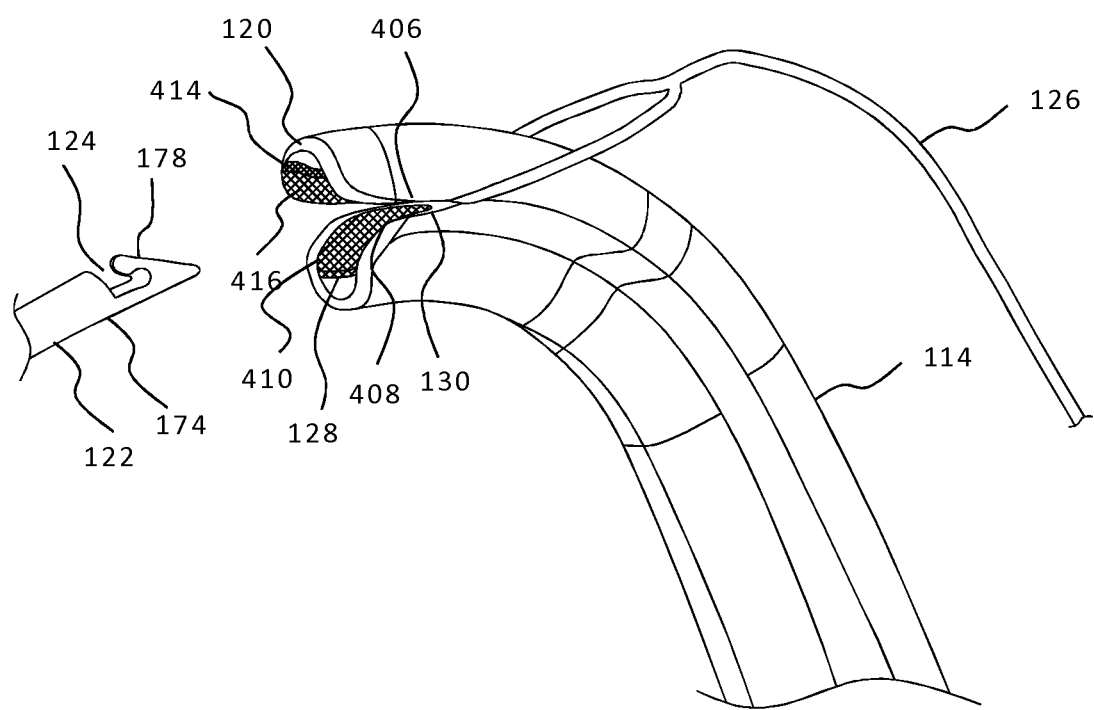
FIG. 4A is a perspective view of a distal end of a needle-receiving arm of the medical device and a tip of the needle.

FIG. 4A is a perspective view of the distal portion of the needle-receiving arm and the tip portion of the needle.

Figure 4B:
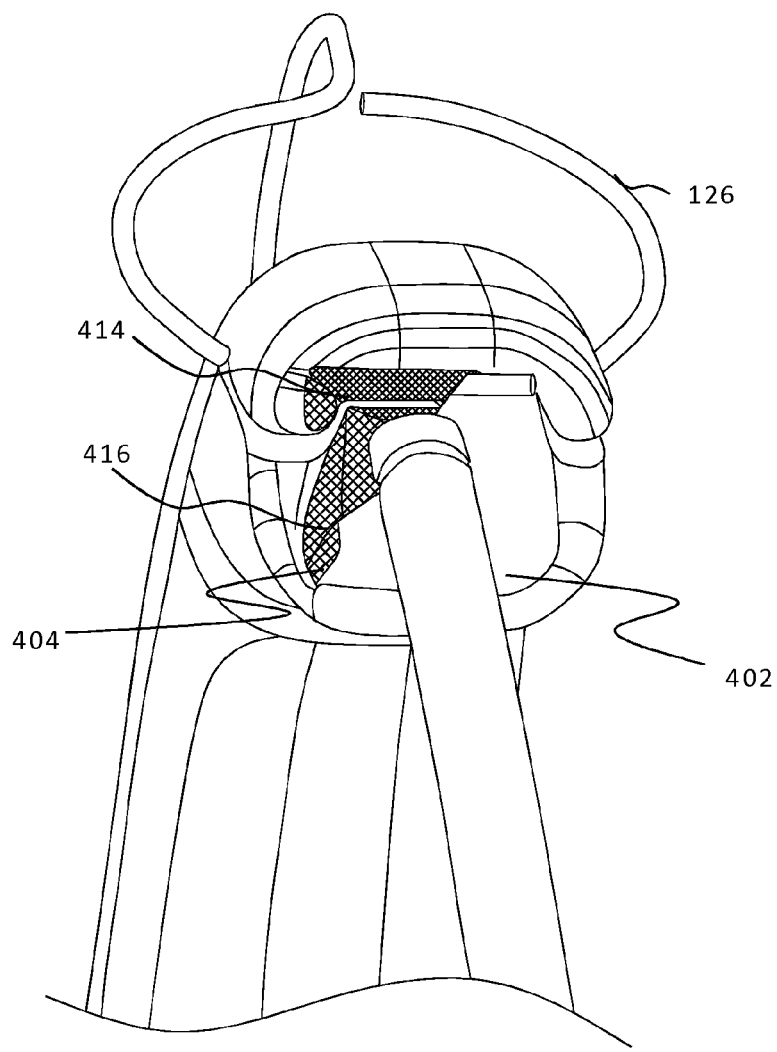
FIGS. 4B-4E are perspective views of the distal end of the needle-receiving arm and the tip of the needle depicting various steps of a needle suture engagement procedure.
Figure 4C:
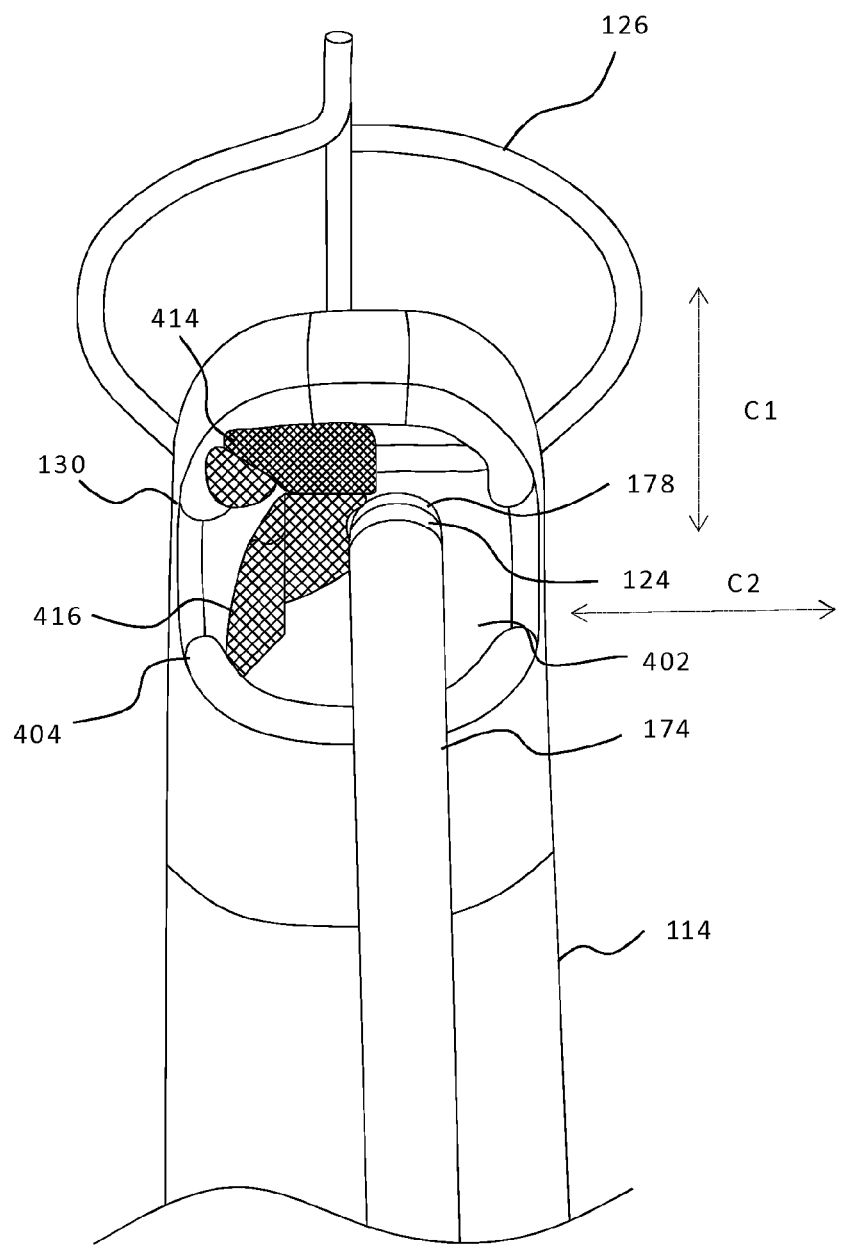

The distal portion 114 of the needle-receiving arm defines the end opening 128 leading to the cavity 120. The distal portion 114 includes a first cavity portion 402 (as shown in FIG. 4B) and a second cavity portion 404 (as shown in FIG. 4B). Each of the first cavity portion 402 and the second cavity portion 404 include the slit 130. The slit 130 is defined by a ceiling edge 406 and a floor edge 408 included in the distal portion 114. The ceiling edge 406 and the floor edge 408 define a slit angle (illustrated in FIG. 4E). The slit 130 can be configured for releasably holding the implant in the cavity 120. The first cavity portion 402 is an open portion or a lumen 410 through which a part of the implant 118 is exposed to the needle 122 for capture.

Figure 4D:
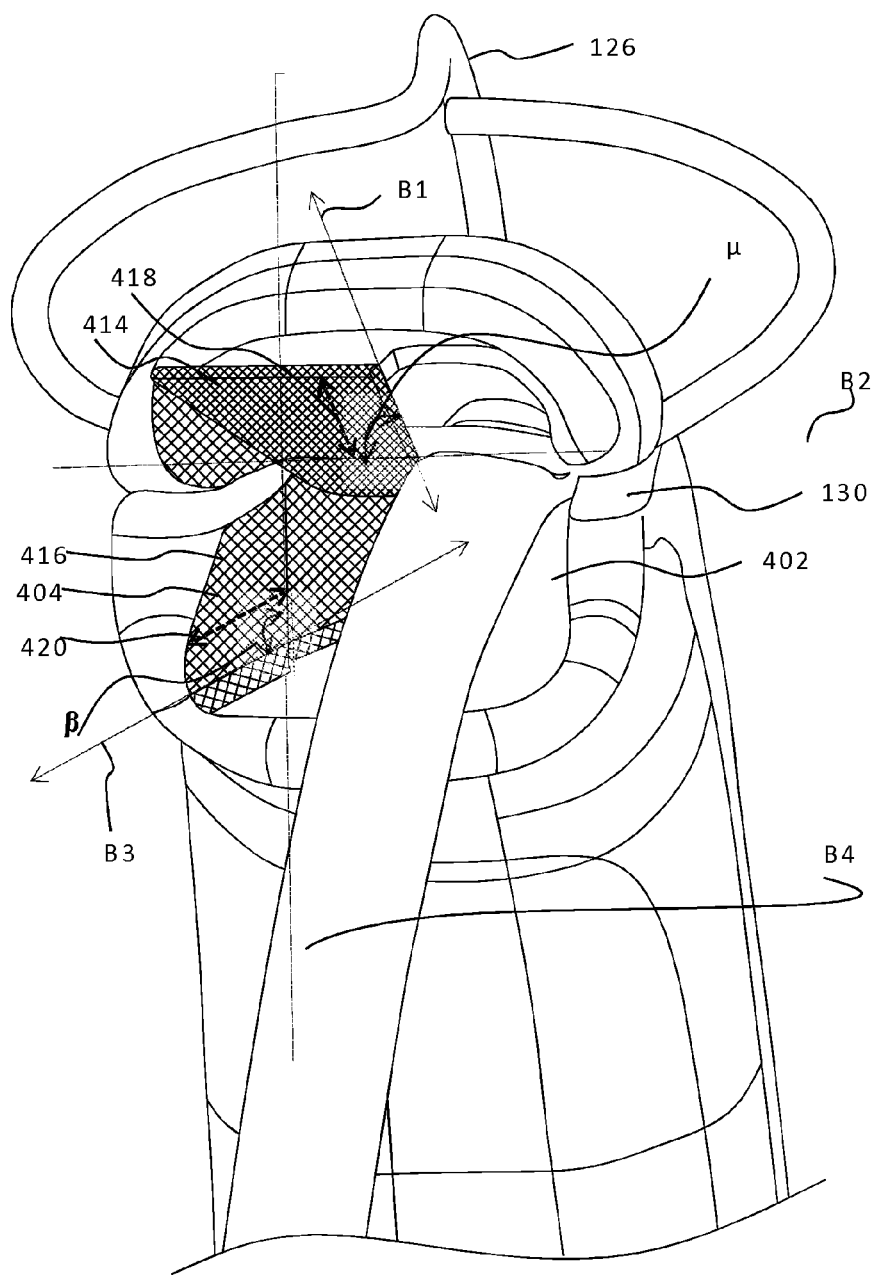
Figure 4E:
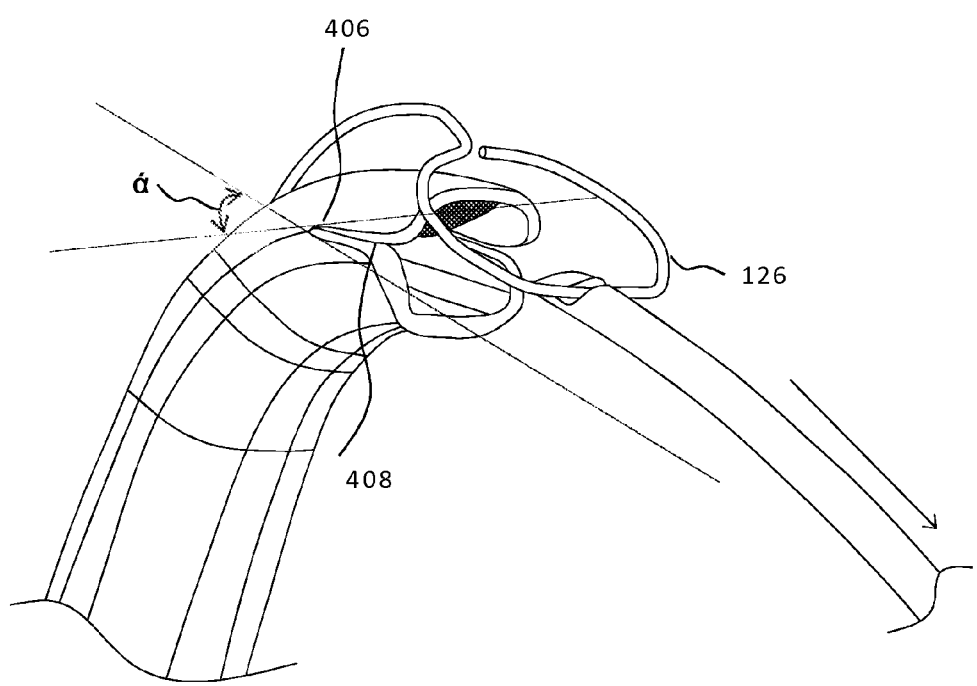

The second cavity portion 404 includes at least two inner walls—a first wall 414 (also referred to as a top ramp 414) and a second wall 416 (also referred to as a side ramp 416) positioned in the second cavity portion 404. The two inner walls 414, 416 are angled with respect to each other to position the needle 122 for capture of the suture 126. The walls 414 and 416 are angled to direct the needle 122 when advanced through the end opening 128 into the first cavity portion 402. The first wall 414 can be fabricated with respect to a plane B1, which makes an angle $\mu$ (as shown in FIG. 4D) with respect to a horizontal plane B2 of the cavity 120. The first wall 414 defines a first slope 418 (as shown in FIG. 4D). The second wall 416 can be fabricated with respect to a plane B3 such that the plane makes an angle $\beta$ with a vertical plane B4 of the cavity 120 such that the second wall 416 defines a second slope 420 (as illustrated in FIG. 4D). The first wall 414 and the second wall 416 can be designed so that the angle $\mu$ is smaller than the angle $\beta$ so that the second slope 420 is greater than the first slope 418. The first slope 420 is configured to guide the needle 122 towards the first cavity portion 402. The second slope 418 is configured to guide the needle 122 below the suture 126. As the second slope 420 is greater than the first slope 418, the movement of the needle 122 towards beneath the suture 126 would be greater than the movement of the needle 122 towards the lumen opening 412. In an embodiment, the tip portion 178 of the needle 122 can be directed downwards and sideways before it is released into the opening of the lumen of the first cavity portion.

The first wall 414 and the second wall 416 are configured to be angled to slideably direct the needle 122 into a position so that the retaining slot 124 of the needle 122 is beneath the suture 126, which can be the end portion of the implant. The end portion or suture 126 of the implant 118 is held across the cavity 120 and is substantially perpendicular to the advanced needle 122.

Referring now to FIGS. 4A-4E, the distal portion 114 of the needle-receiving arm 110 is configured to engage the needle 122 with the implant 118. As a force is applied to the clamping arm 132, the needle 122 moves along the guide rail 154 in the direction A1. The needle 122 can be biased to enter the cavity 120 on application of the force. As the tip portion 178 of the needle 122 advances, the second portion 404 of the cavity 120 can direct the tip portion 178 towards the first portion 402 such that the tip portion 178 of the needle 122 is positioned below the suture 126. This allows the retaining slot 124 to blindly engage with the suture 126. The first wall 414 and the second wall 416 are angled to slidably direct the needle 122 into a position so that the retaining slot 124 of the needle 122 is positioned beneath the end portion of the implant 118. The first wall 414 of the second portion 404 of the cavity 120 can force the needle 122 in a direction C1 towards the open portion of the first cavity portion and the second wall 416 of the second portion 404 can push the needle 122 in a direction C2 so that the needle 122 can be below the suture. As the second slope 420 is greater than the first slope 418, the movement gained by the beveled edge 176 of the tip portion 178 of the needle 122 along the direction C1 would be greater than the movement gained by the tip portion 178 along the direction C2. On continuous application of the force on the needle 122, the first and the second walls 141 and 416 allow the needle 122 to enter the first portion 402 of the cavity 120. As the needle 122 passes the first wall 414 and second wall 416, the needle 122 is configured to spring up towards the suture 126 to capture the suture 126. The first wall 414 of the cavity 120 can be configured to align with the beveled edge 176 of the needle 122. The first wall 414 is aligned to push and direct the needle 122, when the needle 122 is advanced in the cavity 120.

Figure 5A:
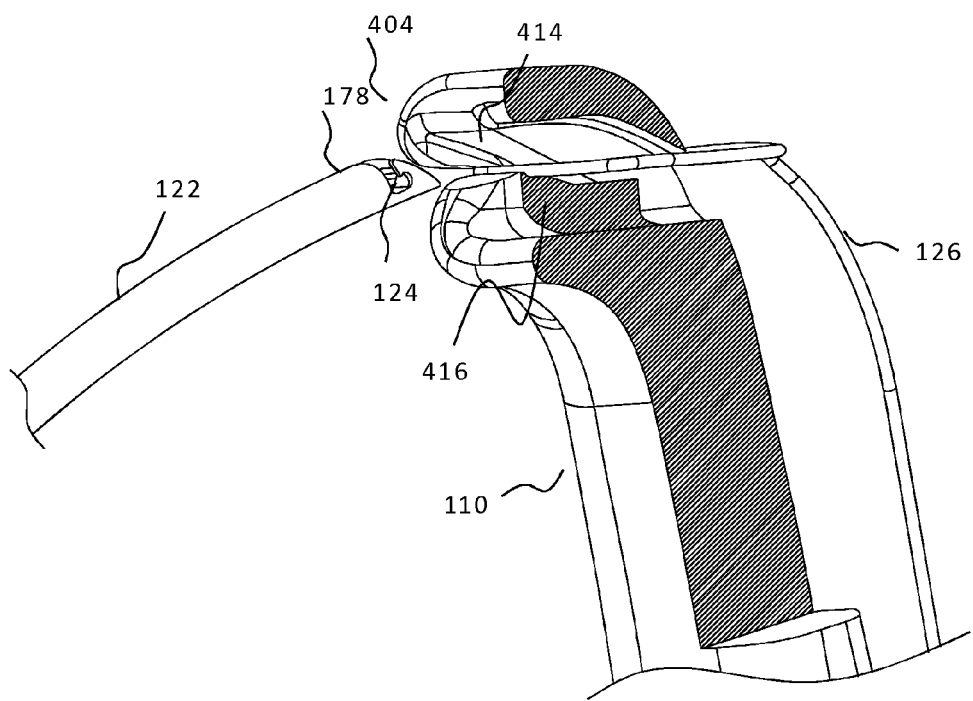
FIG. 5A is a cross-sectional view of a first portion of a cavity of the needle-receiving arm.

FIG. 5A is a cross-sectional view of the second cavity portion 404 of the needle-receiving arm 110, including the first wall 414 and the second wall 416. The walls 414 and 416 are designed such that when the tip portion 178 of the needle 122 springs up, the retaining slot 124 is located right under the suture 126 coupled to the implant 118 (or the suture is the end portion of implant) so that it catches the suture 126. The suture 126 is releasably disposed between the first wall 414 and the second wall 416. In one embodiment, the angles of the first and second walls prevent the needle tip contacting the suture 126, and instead the angled walls direct the needle tip below and past the exposed suture 126. This prevents inadvertent damage to the suture 126 by the needle tip while the needle is advanced into the cavity.

Figure 5B:
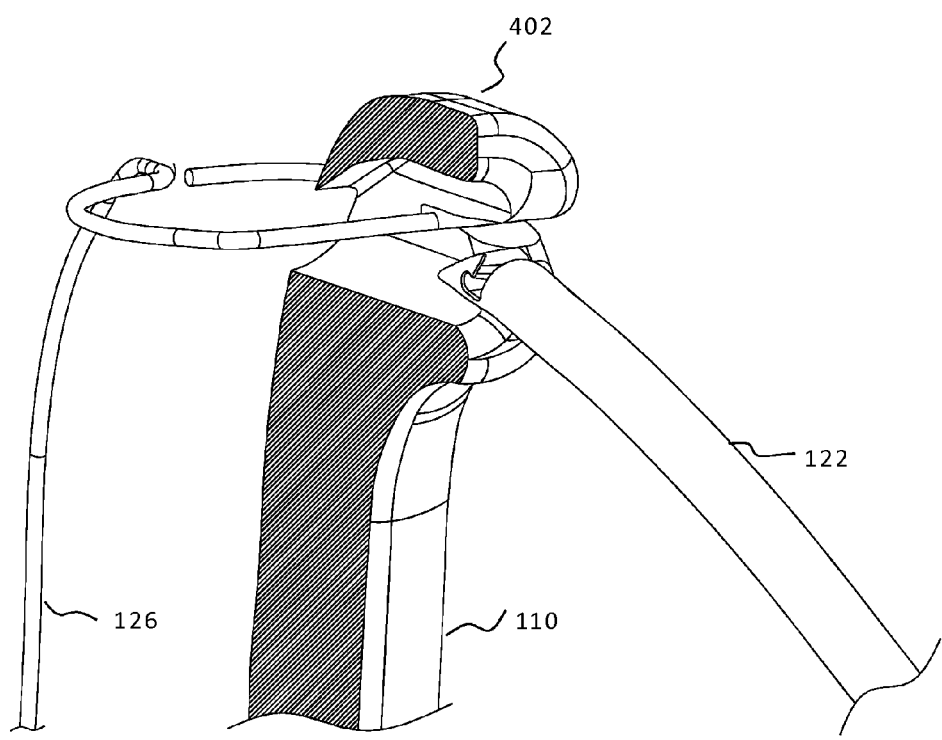
FIG. 5B is a cross-sectional view of a second portion of the needle-receiving arm.

FIG. 5B is a cross-sectional view of the first cavity portion 402 of the needle-receiving arm 110, including an open portion for the needle 122 to advance into the cavity 120 and capture the suture 126. The open space of the first cavity portion 402 exposes the suture to the advancing needle 122.

FIGS. 14A-14G illustrate cross-sectional side views of another embodiment of the distal portion 114 of the needle receiving arm 110 during implant capture. As shown in FIGS. 14A-14G, the needle engages with a suture loop 902 of suture 126 disposed within the needle receiving arm. The suture 126 is coupled to an implant 118 (shown in FIG. 14G). Alternatively, the needle can engage directly with a looped portion that is formed as part of the implant (See FIG. 8). After the needle 122 captures the suture loop 902 in a needle retaining slot 124, the needle 122 retracts and pulls the captured suture 126 and the implant 118 along the needle path. This allows an operator to position the implant 118 in the needle path. The structure of the needle receiving arm 110 and the capture event process as illustrated in FIGS. 14A through 14G are described in more detail below.

Figure 14A:
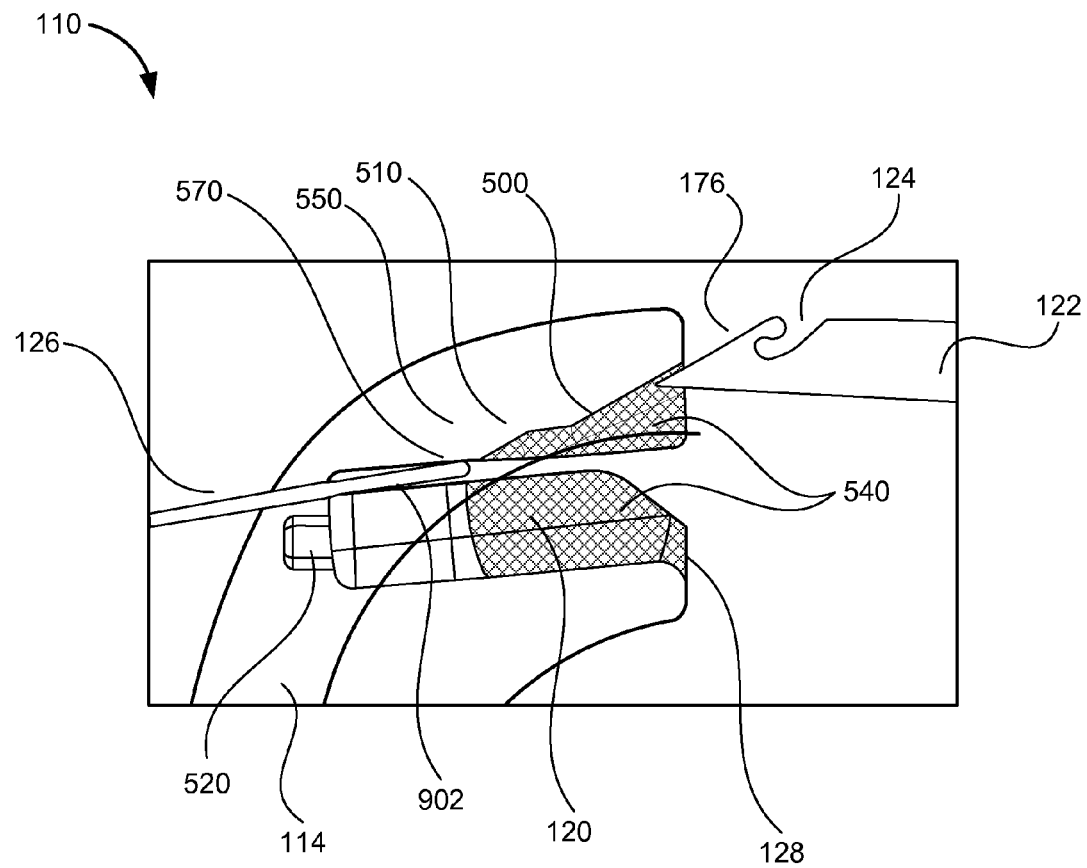
FIGS. 14A-14G illustrate another embodiment of the distal end of the needle receiving arm during the various steps of the needle-suture engagement procedure.

The distal portion 114 of the receiving arm 110, as shown in FIGS. 14A-14G, includes a ceiling wall 550 and one or more other walls 540. As shown, the ceiling wall 550 is a partially angled wall that includes ceiling ramp 500 and a substantially flat portion 570 at the base of the ceiling ramp 500. The ceiling ramp 500 is angled to direct the needle 122 beneath and against the looped end 902 of suture 126 disposed within the cavity 120. In certain embodiments, the ceiling ramp 500 is angled to match fit with the beveled tip 176 of the needle 122. The one or more other walls can be substantially flat (as shown) or angled to direct the needle 122 towards a specific portion of the looped end 902 of the suture 126 disposed within cavity. For example, the one or more other walls 540 can form a funnel-like structure directing the needle 122 to a specific portion of cavity 120. For example, the one or more other walls 540 can be angled to direct the needle 122 to a center portion of the cavity 120 as the needle 122 advances. In another example, the ceiling ramp 500 and the other walls 540 can direct the needle to the center portion of the cavity 120 and in a position such that the needle slides beneath the suture 126 so that the needle 122 slides against the suture 126 during deployment. The looped end 902 of the suture 126 is disposed across the cavity 120 and releasably held between slits 130 such that the suture 126 is substantially perpendicular to the path of the needle 122 and the suture 126 rests against a portion of the ceiling wall 126. Preferably and as shown in FIG. 14A, the suture is tightly held across the cavity so that the suture presses against at the flatter portion 570 of the ceiling wall 550 located at the base of the ceiling ramp 500. Without clearance between the suture 126 and the ceiling wall 550, the suture 126 does not bow or move further into the cavity 120 as the needle 122 passes against the suture 126, but rather the suture 126 is further forced against the ceiling wall 550 when the needle 122 passes against the suture 126. The suture 126 can be held tightly across the cavity by, for example, pulling on the suture 126 or the implant 118 coupled to the suture 126.

Figure 14B:
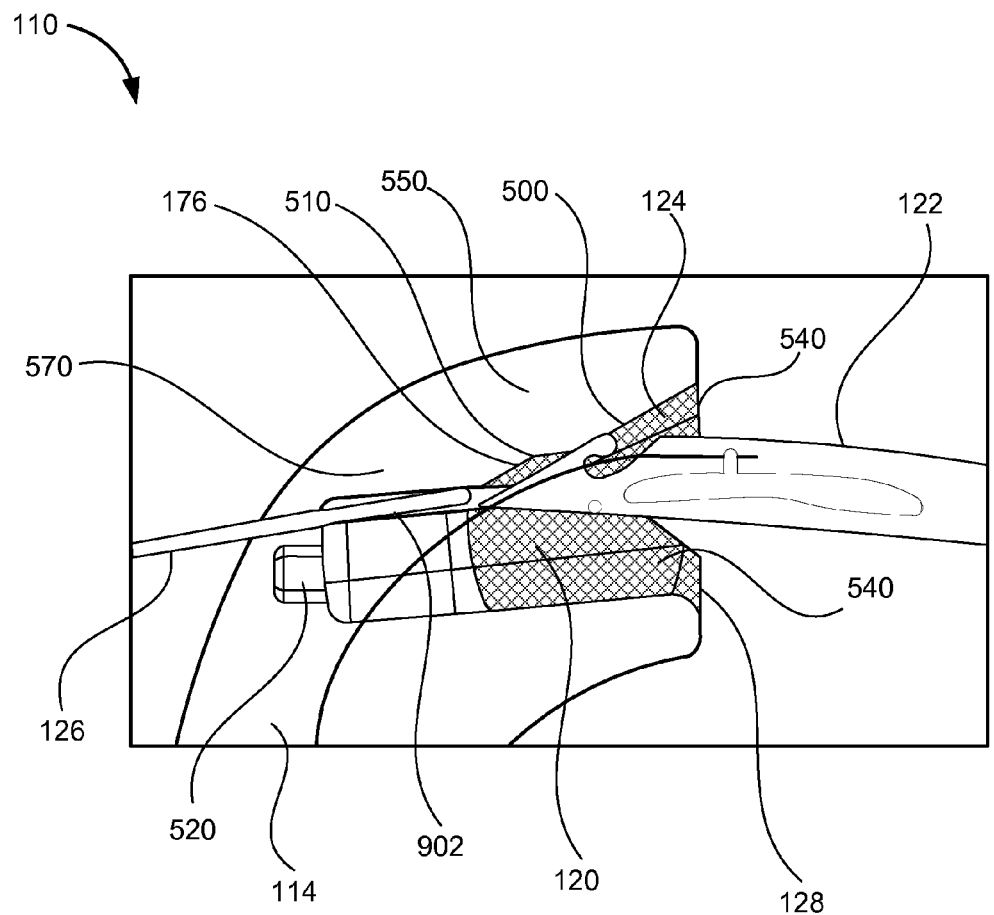
Figure 14C:
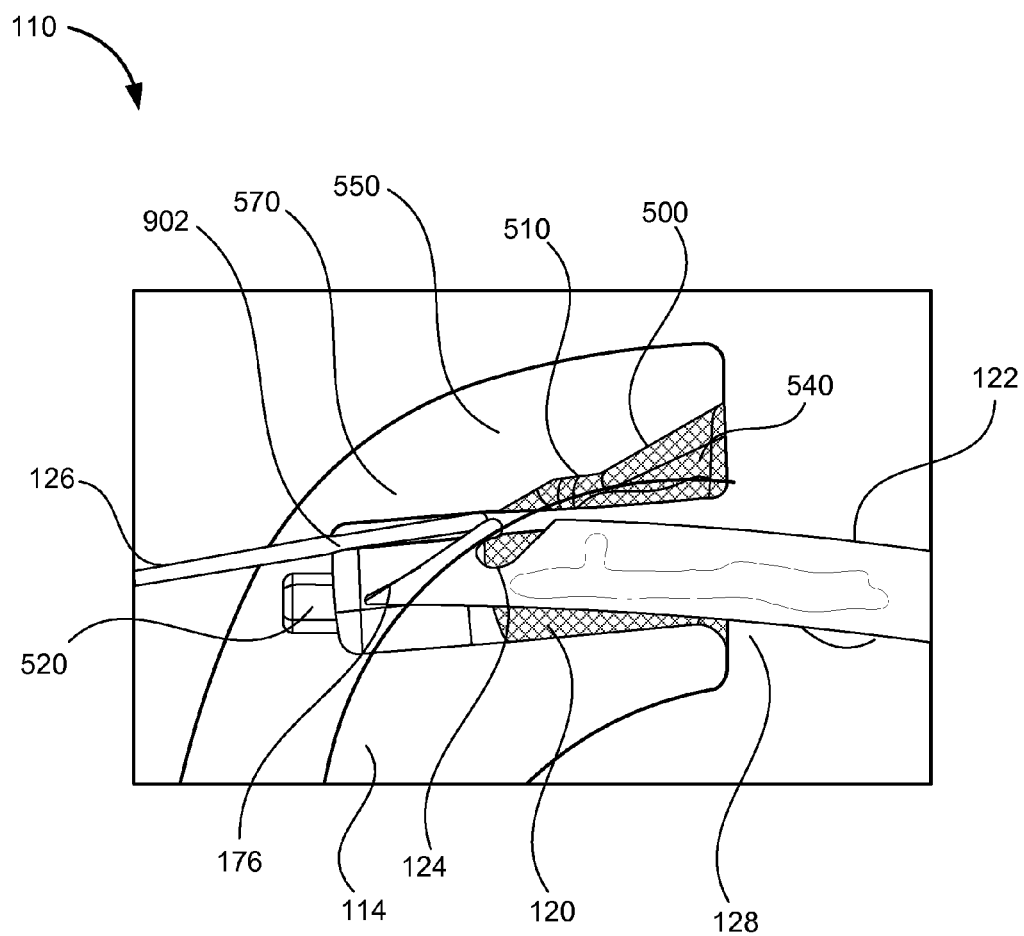
Figure 14D:
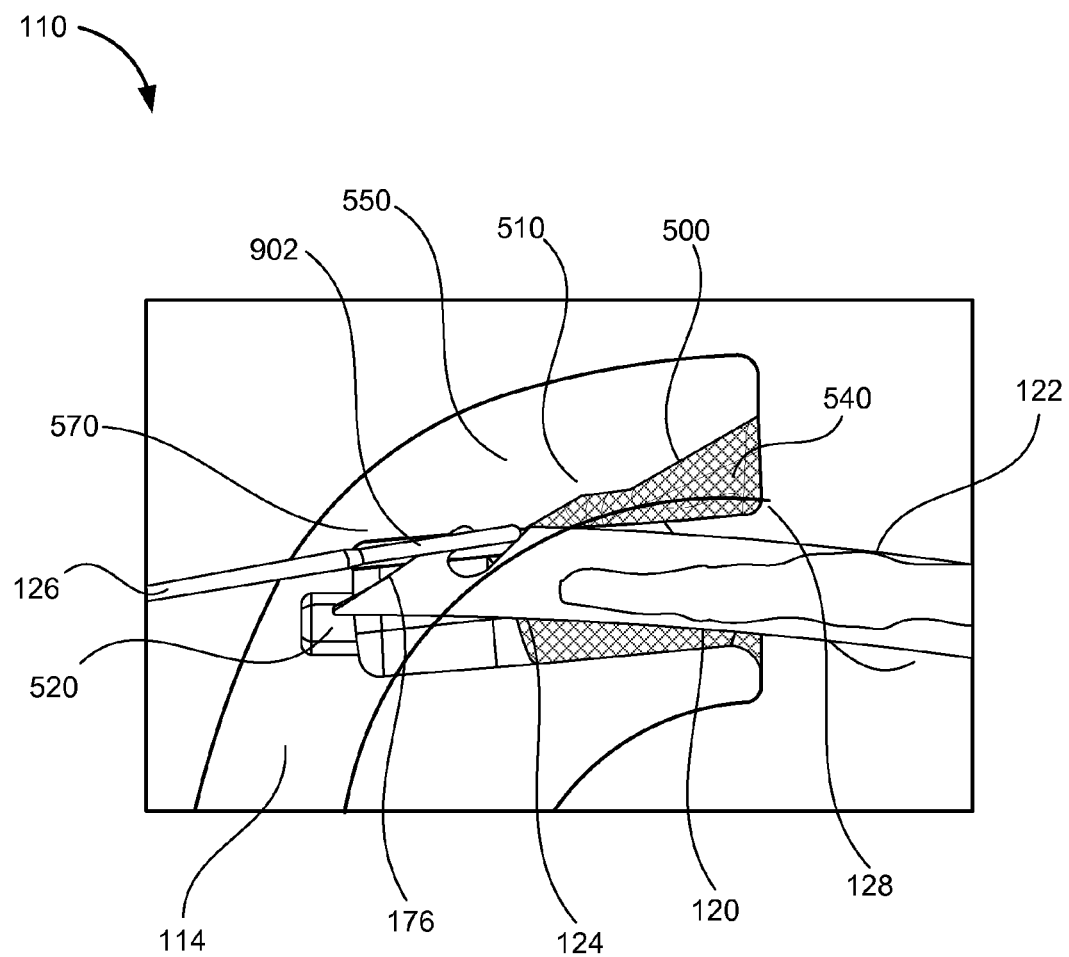
Figure 14E:
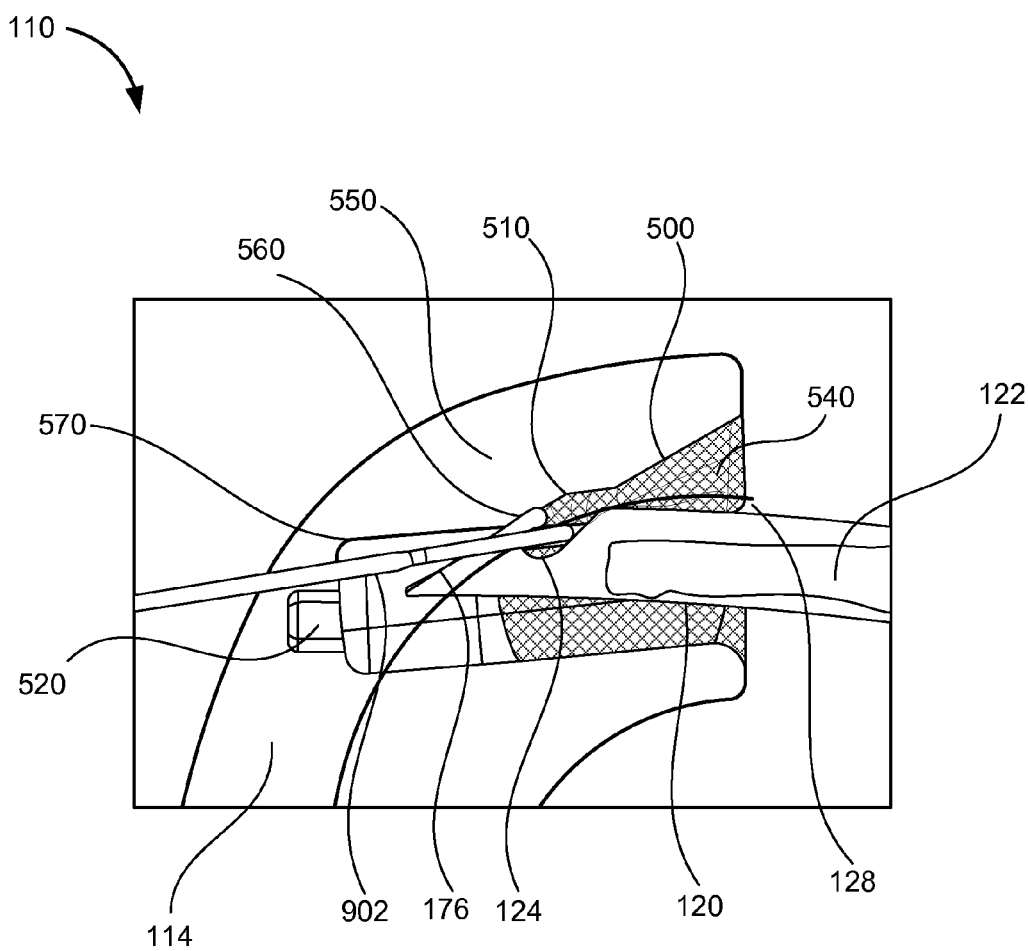
Figure 14F:
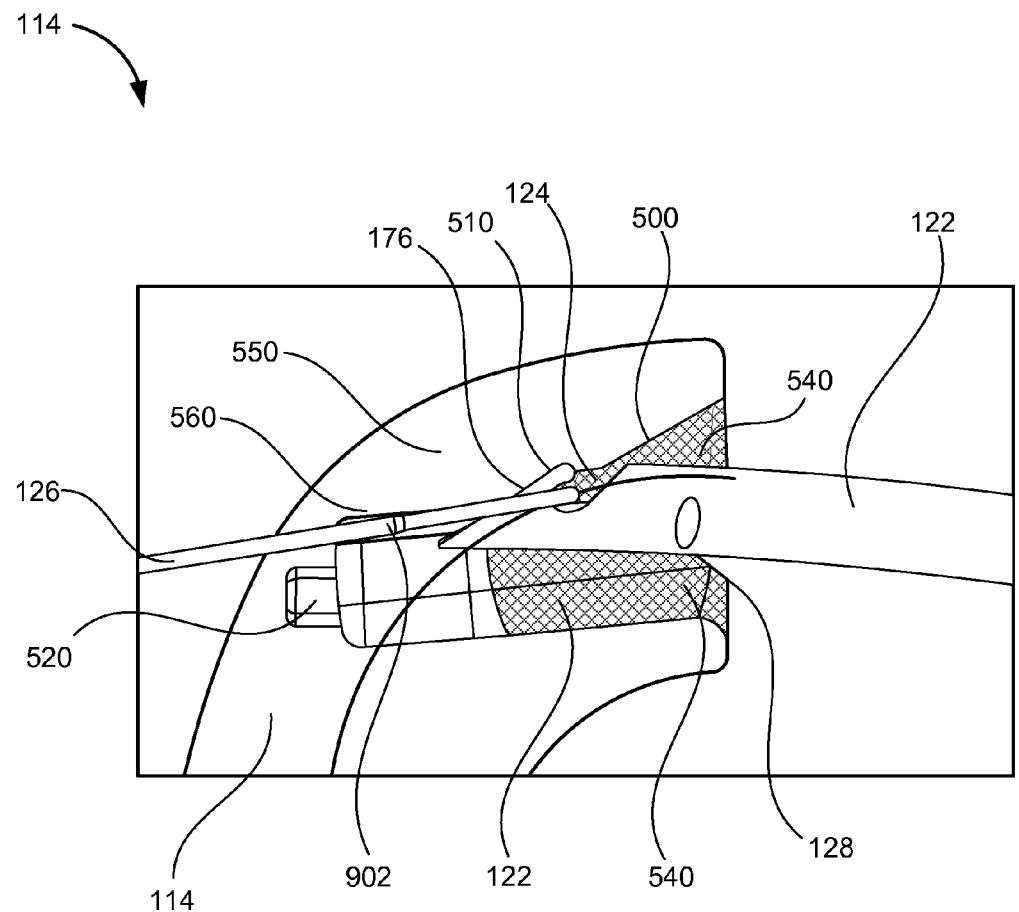
Figure 14G:
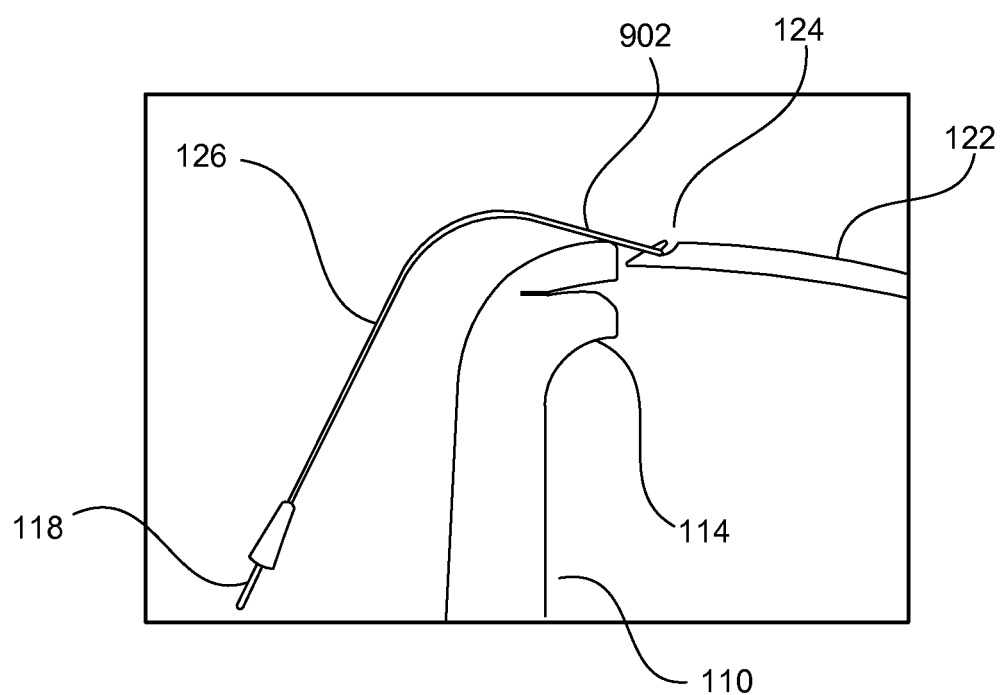

Referring now to the needle-suture engagement process, FIG. 14A depicts the needle 122 as it begins entering the opening 128 of the distal portion 114 of the receiving arm 110. The clamping arm 132 (not shown) directs the needle 122 and into the distal portion 114. As shown, the needle 122 is biased to engage with the ceiling ramp 500. As previously discussed, the guide compartment 140 of the clamping arm 132 may bias the needle 122 during deployment. FIG. 14B shows the needle 122 moving forward within the cavity 120. The beveled tip 176 passes a recess 510 within the ceiling ramp 500. The recess 510 is designed to assist in suture capture as the needle is retracted. However, as the needle 122 moves forward within the cavity 120, it is preferable that the needle 122 does not deviate into recess 510 when sliding against the ceiling ramp 500. To accomplish this, the beveled tip 176 of the needle 126 is designed to be longer than the length of the recess 510. This allows for the needle 122 to pass the recess 510 and engage with the suture 126 while remaining in partial contact with the ceiling ramp 500. As the needle moves forward from the position in FIG. 14B to the position in FIG. 14C, the needle 122 slides beneath and against the suture 126, thus pressing the suture 126 against ceiling wall 550. During deployment, the suture 126 also applies downward pressure on the needle 122, which is upwardly biased. As the needle 122 moves from the position in FIG. 14C to FIG. 14D, the needle retaining slot 124 meets the suture 126, which causes needle 122 to spring upward and forces the suture 124 to enter the needle retaining slot 124. As also shown in FIG. 14D, the tip of the needle 122 does not engage with a back wall of the cavity 120 because the cavity 120 includes a back wall inlet 122. The back wall inlet 122 receives the needle 122 tip and provides the needle 122 with enough clearance within the cavity 120 to ensure capture. With the suture 126 disposed within the needle retaining slot 124, the needle 122 and the captured suture 126 are retracted out of the cavity dragging along the implant 118 (not shown). FIG. 14E shows the needle 122 slightly retracted. In this position, the distal edge 560 of the needle retaining slot 124 of the needle 122 enters into the recess 510 of the ceiling ramp 500. Following the profile of the recess 510, the needle 122 is directed upward which causes the suture 126 to move deeper into the needle retaining slot 124. This enables the needle 122 to obtain a better grasp on the suture 126, thereby increasing the likelihood of successful placement of the implant 118 as it is pulled through tissue via the needle 122 and suture 126. FIG. 14F depicts the needle 122 as it continues to retract following the profile of recess 510 of the ceiling ramp 500. As shown in FIG. 14F, the suture 126 is firmly held and deeply positioned within needle retaining slot 124. FIG. 14G shows the needle 122 positioned outside of the needle receiving arm 110. As the needle 122 continues to retract, the implant 118 is pulled along the path of the needle 122. During operation, the implant 118 would be pulled along the tissue path of the needle 122.

FIGS. 6-11, illustrate the implant 118 to be placed inside the patient's body. The implant 118 includes a first end portion 602, a second end portion 604, and a body 606 composed of biological materials having porous, absorbing, or non-absorbing properties.

Figure 6:
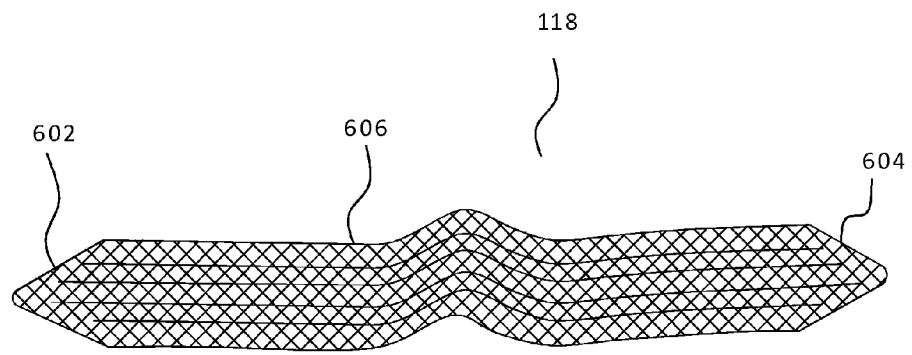
FIG. 6 illustrates an implant to be placed inside a patient's body.

Referring now to FIG. 6, the implant 118 includes the first end portion 602 and the second end portion 604. In an embodiment, the end portions 602 and 604 of the implant 118 can be configured to be attached to a suture such as the suture 126 or a suture or suture-like member 126 is formed as an extension of the implant 118. For example, the suture or suture-like member 126 is the end portion of the implant 118. The suture 126 can be configured to engage with the needle 122. The needle 122 can be retracted after engagement with the suture 126, thereby facilitating the suture 126 and the implant 118 placement inside the patient's body.

Figure 7:
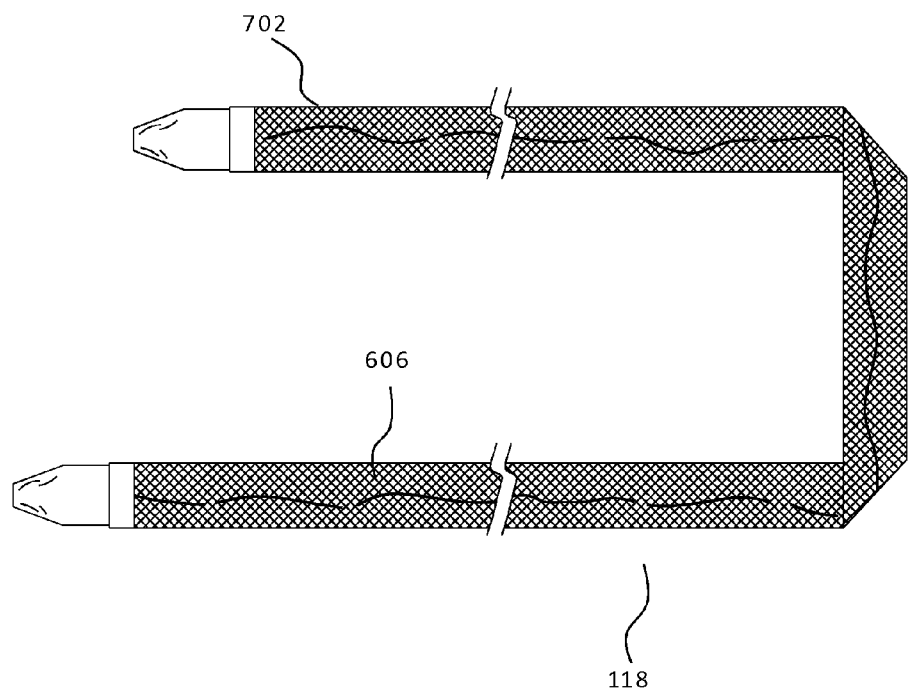
FIG. 7 illustrates an implant including a packaging layer in accordance with an embodiment of the invention.

Referring now to FIG. 7, the body 606 can be configured to include a packaging layer 702, including but not limited to a sheath or a sleeve. In various embodiments the sleeve may cover substantially all of the implant or portion(s) of the implant. The packaging layer 702 is designed to act as a protective sheath for the body 606 of the implant 118. In an embodiment, the end portions 602 and 604 of the implant 118 can be configured to include a portion of the packaging layer 702. The portion of the packaging layer 702 can be configured to connect to at least one of the suture 126 or a similar looped structure (not shown).

Figure 8:
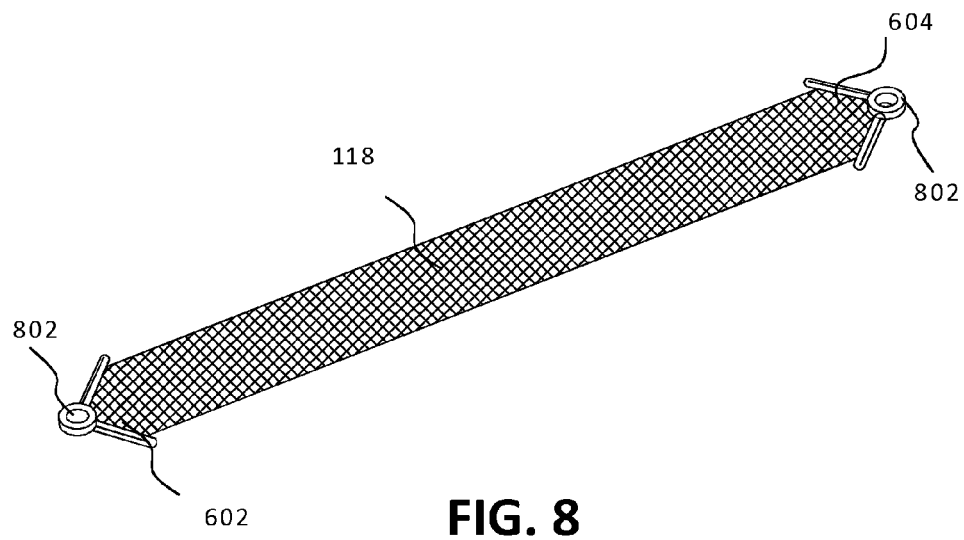
FIG. 8 illustrates an implant including a looped structure in accordance with an embodiment of the invention.

Referring now to FIG. 8, the end portions 602 and 604 of the implant 118 can be configured to include a looped structure 802. In an embodiment, the looped structure 802 of the implant 118 is directly attached to the end portions 602 or 604 of the implant 118. The looped structure 802 of the implant 118 can be configured to directly engage within the slit 130 of the cavity 120.

Figure 9A:
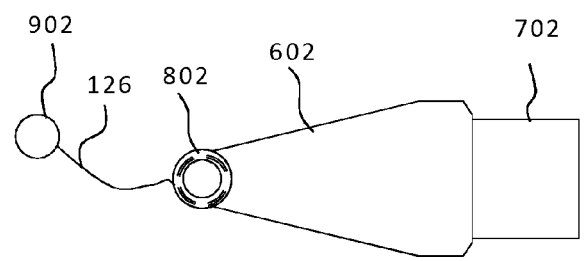
FIGS. 9A-9B illustrate an implant including a looped member in accordance with an embodiment of the invention.
Figure 9B:
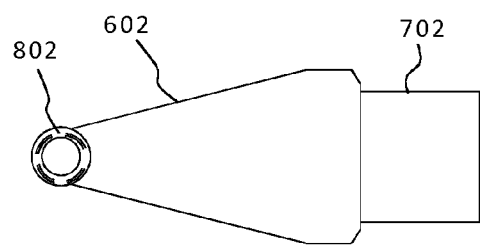

FIGS. 9A and 9B illustrate the end portion 602 and 604 of the implant 118 including the looped structure 802. In an embodiment, the looped structure 802 can be attached to the packaging layer 702 directly. In an embodiment, the looped structure 802 can be configured to be attached to the suture 126 having a looped end 902. The looped structure 802 or the looped end 902 can be designed such as to be releasably held across the slit 130 of the cavity 120. The looped end 802 or looped end 902 are placed to enter into the retaining slot 124 of the needle 122 when the needle 122 advances into the cavity 120.

Figure 10:
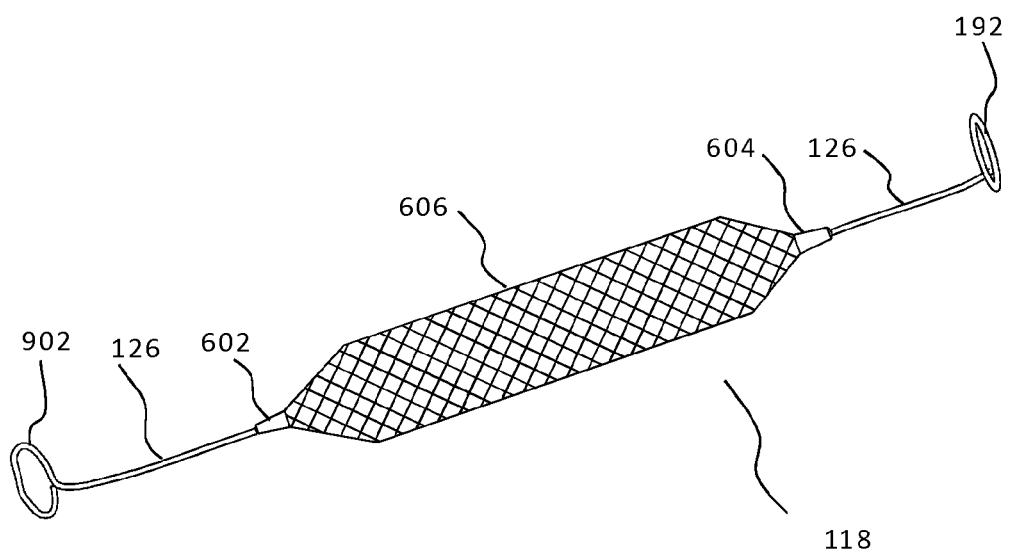
FIG. 10 illustrates an implant including a suture forming a loop at both ends in accordance with an embodiment of the invention.

FIG. 10 illustrates the implant 118 that includes or is coupled to the suture 126 on either sides of the implant 118. The suture 126 is attached at the end portions 602 and 604. The suture can include the looped end 902. In some embodiments, the looped end 902 of the suture 126 is configured to be placed in the slit 130 of the cavity 120.

Figure 11A:
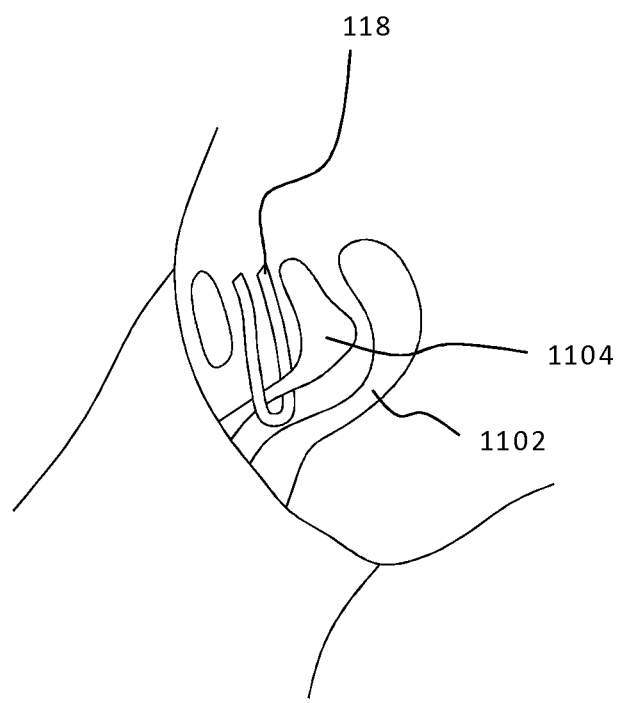
FIG. 11A is a schematic diagram of an implant placed within a patient's body.

FIG. 11A is a schematic diagram of the implant 118 placed within the patient's body. In an embodiment, the implant 118 can be positioned, at least in a part, by the medical device 100 (not shown) between a portion of a vagina 1102 of the patient and a portion of a bladder 1104 of the patient. The implant 118 facilitates in supporting the bladder 1104 of the patient. In an embodiment, the implant 118 can be a sling configured to be implanted into patient's body to such as treat female urinary incontinence by raising or supporting the patient's bladder neck.

Figure 11B:
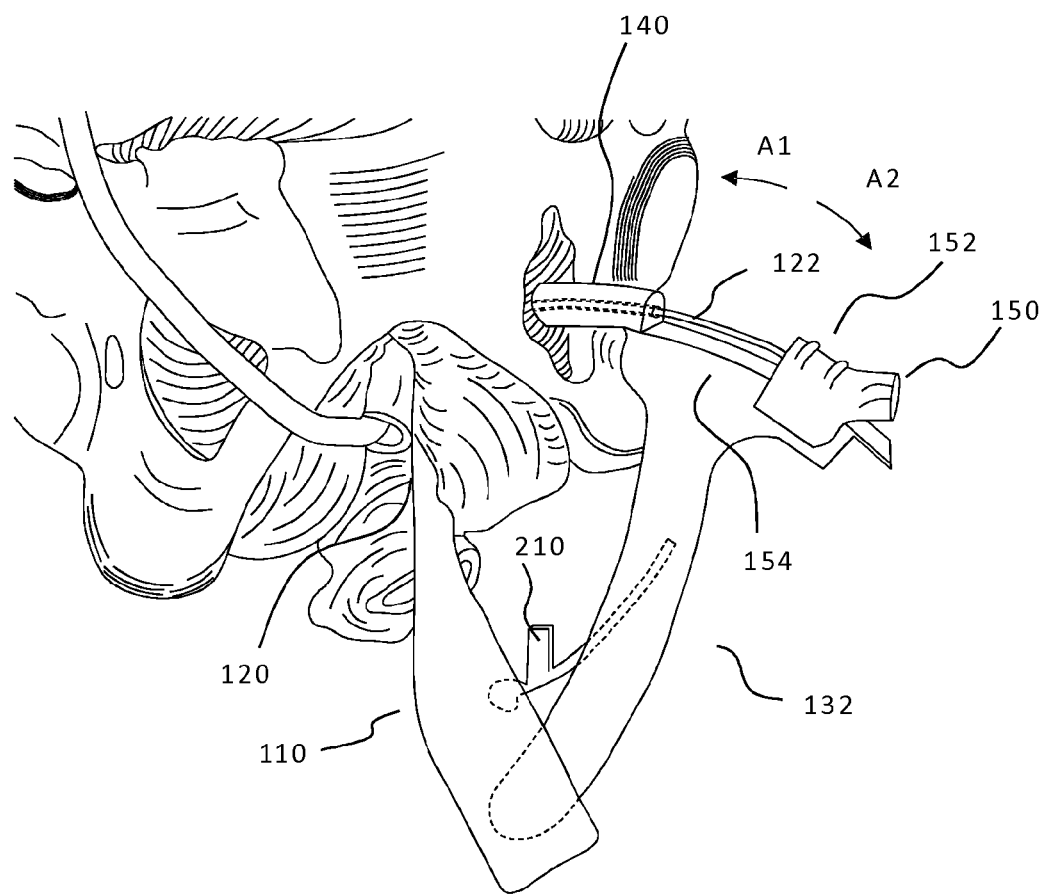
FIG. 11B illustrates a schematic diagram of the implant placed in the pelvic region of the patient.

FIG. 11B schematically illustrates the implant 118 in use with a body portion of a patient. At least a portion of the needle-receiving arm 110 of the medical device 110 is disposed within a vaginal region of the patient's body. The needle-receiving arm 110 has the implant 118 (not shown) attached with it. The clamping arm 132 is in relatively close proximity to an obturator foramen 1106 of the patient. When a force is applied on the sliding component 152, the sliding component 152 gets in a deployed configuration. Further, due to the movement of the sliding component 152, at least a portion of the needle 122 pierces the tissue of the patient to reach the implant 118 attached at the needle-receiving arm 110.

Figure 11C:
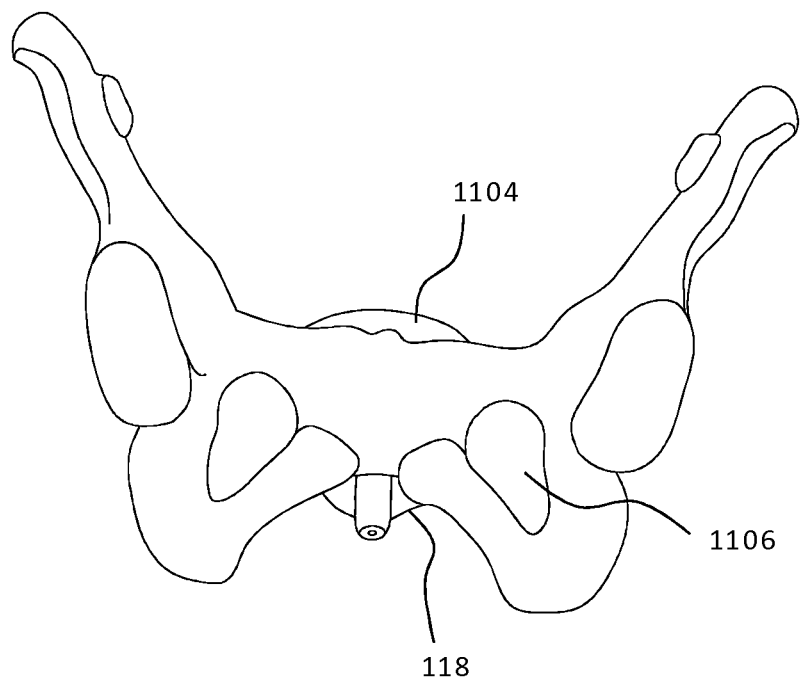
FIG. 11C schematically illustrates the medical device in use with a patient's body.

FIG. 11C illustrates the schematic diagram of the implant 118 placed in the pelvic region of the patient. As illustrated in FIG. 11C, the implant 118 can be placed such that it extends toward the obturator foramen 1106 of the patient. In an embodiment, the implant 118 can be either disposed within or coupled to muscles proximate to the obturator foramen 1106. The medical device 100 can be used to deliver the implant 118 to the pelvic region of the patient via a retropubic or a suprapubic approach, in some embodiments.

Figure 11D:
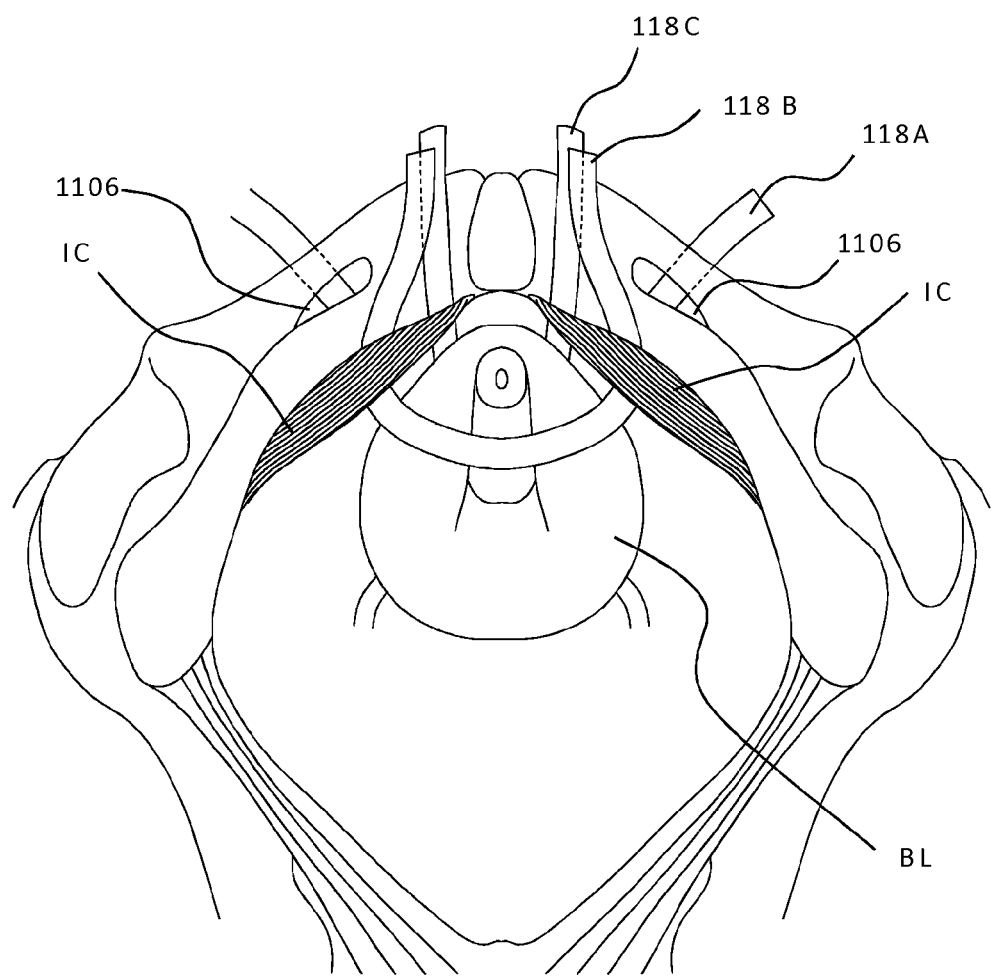
FIG. 11D illustrates a schematic diagram of multiple implants placed within the patient's body.

FIG. 11D illustrates a schematic diagram of multiple implants 118A to 118C placed within the patient's body. The implants 118A and 118C can be positioned at different locations within the patient's body. In this particular embodiment, the implant such as 118A can be placed within the patient's body such that the implant 118A extends through the obturator foramen 1106 of the patient. In an embodiment, the implant 118B can extend between a mid-line incision, ischiocavernosus muscle (IC) and in front of the pubic bone (prepubic approach). In an embodiment the implant 118C can be disposed within the patient's body in a "V" shape. In an embodiment, the implant 118B may extend between the arcus tendineus fascia pelvis (ATFP) and the obturators of the patient.

Figure 12:
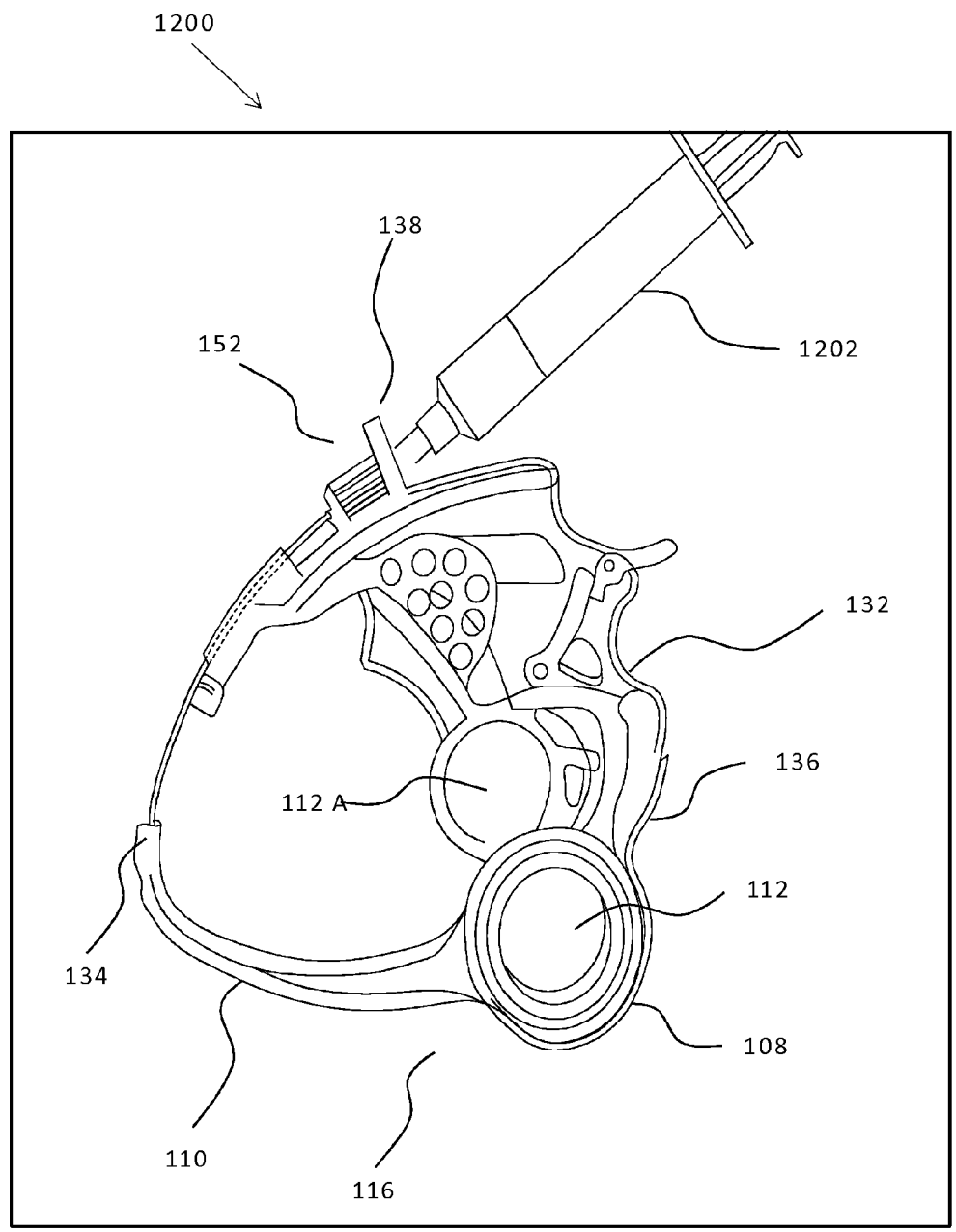
FIG. 12 illustrates a side view of a medical device in accordance with an embodiment of the invention.

FIG. 12 illustrates a perspective view of a medical device 1200 according to an embodiment. The medical device 1200 can be similar to the medical device 100 but can include more than one finger hole 112. In the illustrated embodiment, the medical device 1200 includes two finger holes—112 and 112A. The finger holes 112 and 112A facilitate operational control of the medical device 1200 thereby circumventing the need for the handle 106. The medical device 1200 can be configured to be used as an insertion tool or delivery tool to place the implant 118 in the patient's body similar to the medical device 100. The clamping arm 132 of the medical device 100 can be configured to include a plunger 1202 (interchangeably refer to as a syringe) at the proximal portion 136 of the clamping arm 132. The syringe 1202 functions as the needle deployment mechanism 138. The syringe 1202 is adapted to be pressed for allowing the sliding component 152, attached to the syringe 1202, to move in the direction A1 towards the needle-receiving arm 110.

Figure 13:
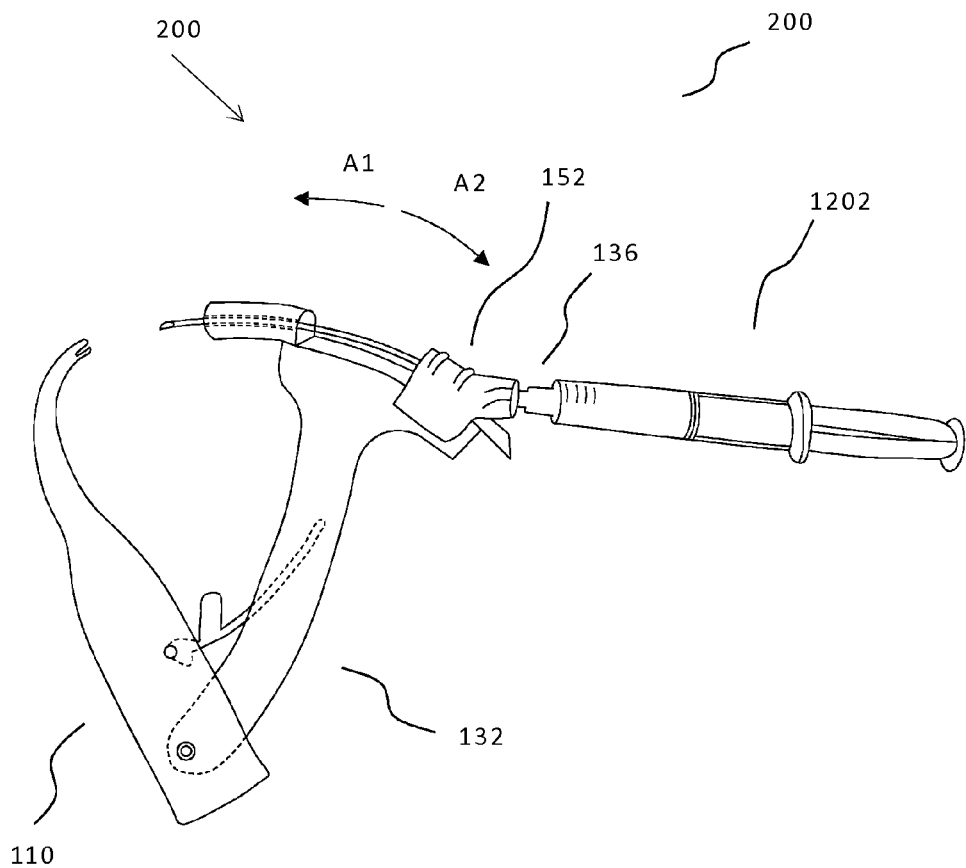
FIG. 13 illustrates a side view of a medical device in accordance with an embodiment of the invention.

FIG. 13 illustrates the perspective view of the medical device 200 with the plunger 1202. The medical device 200 is configured to include the plunger 1202 placed at the proximal portion 136 of the clamping arm 132. Specifically, the syringe 1202 is configured to be attached to the sliding component 152.

While the invention has been disclosed in connection with certain embodiments that are shown and described herein in detail, various modifications and improvements are possible and should be considered to be part of this disclosure.

What is claimed is:

1. A medical device system for delivering one or more implants into a body of a patient, comprising:
    a suture coupled to an implant, the suture including material selected from the group consisting of a metal, a biological material, and a synthetic material;
    a needle having a retaining slot configured to retain the suture;
    a needle-receiving arm, at least a portion of the needle-receiving arm being curved, the needle-receiving arm including a distal end portion configured to releasably hold the suture, the distal end portion defining an end opening leading to a cavity for receiving the needle, the cavity having at least two inner walls angled to direct the needle, when advanced through the end opening and into the cavity, into a position where the suture is configured to be disposed in the retaining slot of the needle; and
    a clamping arm movably coupled to the needle-receiving arm, at least a portion of the clamping arm being curved, the clamping arm having comprising a needle deployment mechanism for advancing the needle through tissue of the body of the patient and into the cavity of the distal end portion of the needle-receiving arm to allow the suture to be disposed in the retaining slot of the needle, the needle deployment mechanism of the clamping arm also for retracting the needle out of the cavity of the needle-receiving arm back through the tissue to pull the suture that is disposed in the retaining slot of the needle through the tissue.

2. The medical device of claim 1 wherein the suture is a suture loop that is releasably held by the distal end portion of the needle-receiving arm.

3. The medical device of claim 1 wherein the suture extends from one end of the implant.

4. The medical device of claim 1 wherein the suture extends from one end of a packaging in which the implant is contained.

5. The medical device of claim 1 wherein the implant is a sling configured for implantation into the body of the patient to treat female urinary incontinence by raising or supporting the patient's bladder neck.

6. The medical device of claim 1 wherein the needle deployment mechanism includes a sliding component and a curved guide rail, the sliding component coupled to the needle such that movement of the sliding component translates into movement of the needle, the sliding component moveably coupled to the curved guide rail to allow an operator to manually move the sliding component distally along the curved guide rail to advance the needle and to manually move the sliding component proximally along the curved guide rail to retract the needle.

7. The medical device of claim 6 wherein the sliding component comprises a grasping element for manually moving the sliding component along the curved guide rail.

8. The medical device of claim 7 wherein the grasping element is coupled to a syringe operably associated with the needle.

9. The medical device of claim 6 wherein the clamping arm further comprises a guide compartment located distal to the needle deployment mechanism, the guide compartment comprising a lumen through which the needle passes as the needle is advanced and retracted, the guide compartment assisting in biasing the needle towards the cavity.

10. The medical device of claim 6 wherein movement of the sliding component is independent from movement of the clamping arm.

11. The medical device of claim 1 wherein the at least two angled walls comprise a first wall and second wall angled to slideably direct the needle into a position so that the retaining slot of the needle is beneath the suture when the needle passes the first and second angled walls, the needle being configured to spring up towards the suture, upon passing the first and second angled walls, to dispose the suture into the retaining slot of the needle.

12. The medical device of claim 1 wherein the distal end portion of the needle-receiving arm further comprises a first slit and a second slit for releaseably holding the suture in the cavity.

13. The medical device of claim 1, wherein the suture is held across the cavity and substantially perpendicular to the needle.

14. The medical device of claim 1 wherein the needle comprises a beveled tip configured to align with the angle of at least one of the at least two walls.

15. A medical device system for delivering one or more implants into a body of a patient, comprising:
    a suture coupled to an implant;
    a needle having a retaining slot;
    a needle-receiving arm, at least a portion of the needle-receiving arm being curved, the needle-receiving arm having a distal end portion configured to releasably hold the suture, the distal end portion defining an end opening leading to a cavity for receiving the needle, the cavity defining a first cavity portion and a second cavity portion, the first cavity portion defining a lumen through which a part of the suture is exposed to an interior of the first cavity portion, the second cavity portion having at least two inner walls angled to move the needle, when advanced through the end opening, into the interior of the first cavity portion such that the suture is captured in the retaining slot of the needle; and a clamping arm movably coupled to the needle-receiving arm, at least a portion of the clamping arm being curved, the clamping arm having a needle deployment mechanism and a guide compartment distal to the needle deployment mechanism, the guide compartment having a longitudinal axis and defining a lumen through which the needle passes as the needle is advanced and retracted, the guide compartment configured for biasing the needle towards the second cavity portion of the needle-receiving arm, the needle deployment mechanism for advancing the needle into the guide compartment, through tissue, and into the cavity of the distal end portion of the needle-receiving arm to allow the suture to be captured in the retaining slot of the needle, the needle deployment mechanism of the clamping arm also for retracting the advanced needle and the suture out of the cavity and through the tissue.

16. The medical device of claim 15 wherein the suture is is a suture loop that is releasably held by the distal end portion of the needle-receiving arm.

17. The medical device of claim 15 wherein the suture extends from one end of the implant.

18. The medical device of claim 15 wherein the suture extends from one end of a packaging in which the implant is contained.

19. The medical device of claim 15 wherein the implant is a sling configured for implantation into the body of the patient to treat female urinary incontinence by raising or supporting the patient's bladder neck.

* * * * *